(12) United States Patent
Wine

(10) Patent No.: US 12,721,989 B2
(45) Date of Patent: Sep. 1, 2026

(54) CONNECTOR COUPLING ASSEMBLY

(71) Applicant: CareFusion 303, Inc., San Diego, CA (US)

(72) Inventor: Jason Andrew Wine, Brea, CA (US)

(73) Assignee: CAREFUSION 303, INC., San Diego, CA (US)

( * ) Notice: Subject to any disclaimer, the term of this patent is extended or adjusted under 35 U.S.C. 154(b) by 333 days.

(21) Appl. No.: 18/525,166

(22) Filed: Nov. 30, 2023

(65) Prior Publication Data

US 2024/0204452 A1 Jun. 20, 2024

Related U.S. Application Data

(60) Provisional application No. 63/432,666, filed on Dec. 14, 2022.

(51) Int. Cl.
*A61M 39/10* (2006.01)

(52) U.S. Cl.
CPC . *A61M 39/1011* (2013.01); *A61M 2039/1033* (2013.01); *A61M 2039/1061* (2013.01)

(58) Field of Classification Search
CPC ...... A61M 39/1011; A61M 2039/1033; A61M 2039/1061
See application file for complete search history.

(56) References Cited

U.S. PATENT DOCUMENTS

| | | | |
|---|---|---|---|
| 5,713,856 | A | 2/1998 | Eggers et al. |
| 6,874,522 | B2 | 4/2005 | Anderson et al. |
| 7,004,934 | B2 | 2/2006 | Vaillancourt |
| 7,040,598 | B2 | 5/2006 | Raybuck |
| 7,153,296 | B2 | 12/2006 | Mitchell |
| 7,350,764 | B2 | 4/2008 | Raybuck |

(Continued)

FOREIGN PATENT DOCUMENTS

| | | |
|---|---|---|
| EP | 1678070 A2 | 7/2006 |
| EP | 1517723 B1 | 1/2007 |

(Continued)

OTHER PUBLICATIONS

International Search Report and Written Opinion for Application No. PCT/US2023/081002, dated Mar. 14, 2024, 11 pages.

(Continued)

*Primary Examiner* — Zachary T Dragicevich
(74) *Attorney, Agent, or Firm* — MASCHOFF BRENNAN

(57) ABSTRACT

A coupler including a first connector having a first end, a second end opposite the first end, and a valve extending from an area proximate the second end to an area proximate the first end, a second connector having a mating portion and a connecting portion opposite the mating portion, and a collar having a connecting end detachably coupled to the mating portion and an engaging end disposed opposite the connecting end, the collar including a thread detachably coupled to the engaging end the thread configured to couple to at least a portion of the first connector to detachably couple the first connector to the collar and the second connector, such that the first connector, the collar, and the second connector form a fluid pathway. The first connector and the thread are configured to decouple from the collar while the collar remains coupled to the second connector.

20 Claims, 18 Drawing Sheets

(56) References Cited

U.S. PATENT DOCUMENTS 7,396,051 B2 7/2008 Baldwin et al.
7,763,013 B2 7/2010 Baldwin et al.
7,766,394 B2 8/2010 Sage et al.
7,794,675 B2 9/2010 Lynn
7,803,139 B2 9/2010 Fangrow, Jr.
7,803,140 B2 9/2010 Fangrow, Jr.
7,815,614 B2 10/2010 Fangrow, Jr.
7,918,243 B2 4/2011 Diodati et al.
7,998,134 B2 8/2011 Fangrow et al.
8,123,738 B2 2/2012 Vaillancourt
8,142,418 B2 3/2012 Mcmichael et al.
8,211,069 B2 7/2012 Fangrow, Jr.
8,262,628 B2 9/2012 Fangrow, Jr.
8,361,408 B2 1/2013 Lynn
8,480,968 B2 7/2013 Lynn
8,777,908 B2 7/2014 Fangrow, Jr.
8,777,909 B2 7/2014 Fangrow, Jr.
8,795,256 B1 8/2014 Smith
8,888,758 B2 11/2014 Mansour
8,899,267 B2 12/2014 Diodati et al.
8,910,919 B2 12/2014 Bonnal et al.
8,974,425 B2 3/2015 Tachizaki et al.
8,974,437 B2 3/2015 Williams et al.
9,114,242 B2 8/2015 Fangrow et al.
9,126,028 B2 9/2015 Fangrow et al.
9,126,029 B2 9/2015 Fangrow et al.
9,192,753 B2 11/2015 Lopez et al.
9,234,616 B2 1/2016 Carrez et al.
9,358,379 B2 6/2016 Fangrow, Jr.
9,433,769 B2 9/2016 Bayly
9,468,749 B2 10/2016 Mansour et al.
9,492,649 B2 11/2016 Carrez et al.
9,636,492 B2 5/2017 Fangrow, Jr.
9,724,504 B2 8/2017 Fangrow, Jr. et al.
9,724,505 B2 8/2017 Williams et al.
9,861,805 B2 1/2018 Dennis et al.
9,933,094 B2 4/2018 Fangrow
9,974,939 B2 5/2018 Fangrow, Jr.
9,974,940 B2 5/2018 Fangrow, Jr.
10,029,086 B2 7/2018 Nowak et al.
10,156,306 B2 12/2018 Fangrow
10,173,045 B2 1/2019 Mansour
10,179,203 B1 1/2019 Huslage et al.
10,315,025 B2 6/2019 Phillips et al.
10,398,887 B2 9/2019 Fangrow, Jr. et al.
10,441,507 B2 10/2019 Sanders
10,518,078 B2 12/2019 Stjernberg Bejhed et al.
10,569,073 B2 2/2020 Hallisey et al.
10,625,068 B2 4/2020 Leuthardt et al.
10,655,768 B2 5/2020 Jones et al.
10,697,570 B2 6/2020 Fangrow
10,744,315 B2 8/2020 Sanders
10,842,982 B2 11/2020 Fangrow, Jr.
10,857,346 B2 12/2020 Dennis et al.
10,864,362 B2 12/2020 Jones et al.
10,881,847 B2 1/2021 Lynn
11,168,818 B2 11/2021 Fangrow
11,207,514 B2 12/2021 Kakinoki
11,235,135 B2 2/2022 Tsai
11,273,297 B2 3/2022 Kakinoki
11,484,471 B2 11/2022 Sanders
11,491,084 B2 11/2022 Ueda et al.
2004/0215158 A1 10/2004 Anderson
2005/0090805 A1 4/2005 Shaw et al.
2006/0129109 A1 6/2006 Shaw et al.
2007/0088292 A1 4/2007 Fangrow, Jr.
2007/0088293 A1 4/2007 Fangrow, Jr.
2007/0088294 A1 4/2007 Fangrow, Jr.
2007/0225635 A1 9/2007 Lynn
2008/0039803 A1 2/2008 Lynn
2011/0106046 A1 5/2011 Hiranuma
2014/0249487 A1 9/2014 Lynn
2014/0330254 A1 11/2014 Rosenberger et al.
2016/0000363 A1 1/2016 Jones et al.
2017/0036007 A1 2/2017 Hallisey et al.
2018/0200147 A1 7/2018 Sanders
2018/0221641 A1* 8/2018 Buchanan ............. A61M 39/20
2019/0184152 A1 6/2019 Kakinoki
2019/0282797 A1 9/2019 Tsai
2020/0113784 A1 4/2020 Lopez et al.
2020/0179672 A1 6/2020 Kakinoki
2020/0215319 A1 7/2020 Fangrow, Jr. et al.
2020/0284385 A1 9/2020 Fangrow
2020/0323734 A1 10/2020 Ueda et al.
2020/0338331 A1 10/2020 Sanders
2021/0069484 A1 3/2021 Tsai
2021/0077803 A1 3/2021 Lynn
2021/0252267 A1 8/2021 Fangrow, Jr.
2021/0388926 A1 12/2021 Martin et al.
2021/0393938 A1 12/2021 Lynn et al.
2022/0260189 A1 8/2022 Deuse
2022/0282814 A1 9/2022 Fangrow
2022/0288378 A1 9/2022 Mermelshtein et al.

FOREIGN PATENT DOCUMENTS

EP 1622675 B1 8/2009
EP 2144634 A1 1/2010
EP 2298407 A1 3/2011
EP 2694132 A1 2/2014
EP 2562456 B1 6/2014
EP 2782633 A1 10/2014
EP 1842002 B1 4/2015
EP 2736582 B1 5/2015
EP 2089094 B1 1/2016
EP 2219721 B1 12/2017
EP 2753396 B1 12/2017
EP 2736584 B1 4/2018
EP 3305361 A1 4/2018
EP 2271398 B1 11/2018
EP 2480281 B1 11/2018
EP 2790750 B1 11/2018
EP 2331191 B1 3/2019
EP 3079756 B1 3/2019
EP 2121114 B1 5/2019
EP 2719419 B1 5/2019
EP 2956204 B1 8/2019
EP 3421077 B1 8/2019
EP 3530313 A1 8/2019
EP 3538201 A1 9/2019
EP 3570807 A1 11/2019
EP 3570809 A1 11/2019
EP 2536463 B1 4/2020
EP 3381505 B1 5/2020
EP 3538201 B1 5/2020
EP 1904152 B1 12/2020
EP 2150307 B1 12/2020
EP 3313490 B1 1/2021
EP 3760275 A1 1/2021
EP 3851155 A1 7/2021
EP 3517164 B1 9/2021
EP 3954355 A1 2/2022
EP 3960229 A1 3/2022
EP 3973044 A1 3/2022
EP 3305361 B1 5/2022
EP 3134052 B1 8/2022
EP 3530313 B1 8/2022
WO WO-2021099437 A1 5/2021
WO WO-2021180675 A1 9/2021
WO WO-2021252197 A1 12/2021
WO WO-2022042956 A1 3/2022
WO WO-2022149339 A1 7/2022
WO WO-2022207560 A1 10/2022

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.

Icumedical, "ChemoClave™ Needlefree Close System Transfer Device (CSTD)", date unknown, https://www.icumed.com/products/oncology/closed-system-transfer-devices/chemoclave.

(56) References Cited

OTHER PUBLICATIONS

Icumedical, "ChemoLock™ Needlefree Closed System Transfer Device (CSTD)", date unknown, https://www.icumed.com/products/oncology/closed-system-transfer-devices/chemolock.
Ivteam, "Force-activated separation IV connectors", 2022, Retrieved from the internet https://www.ivteam.com/intravenous-literature/force-activated-separation-iv-connectors/ [Last retrieved Jan. 13, 2023].
Lineus Medical, SafeBreak Product Features and Benefits Brochure, May 2021, mkg 0058 May 2021 Rev. 02.
Przen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].
Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.
Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].
Tribology, "Coefficient of friction, Rolling resistance and Aerodynamics", date unknown, https://www.tribology-abc.com/abc/cof.htm.

* cited by examiner

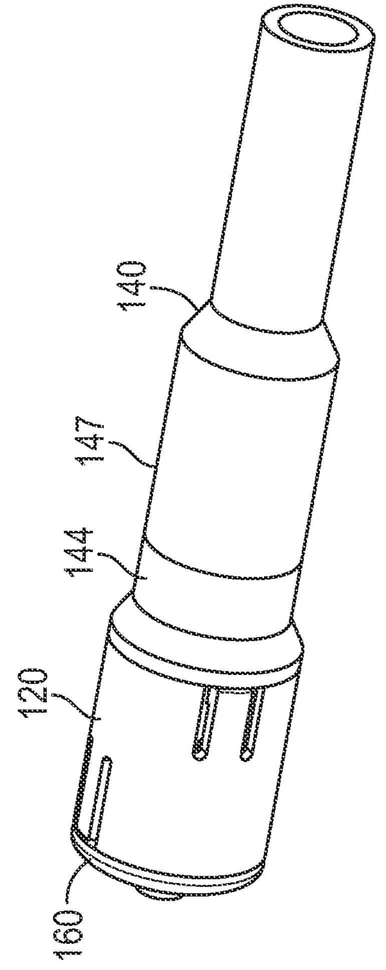
FIG. 2A
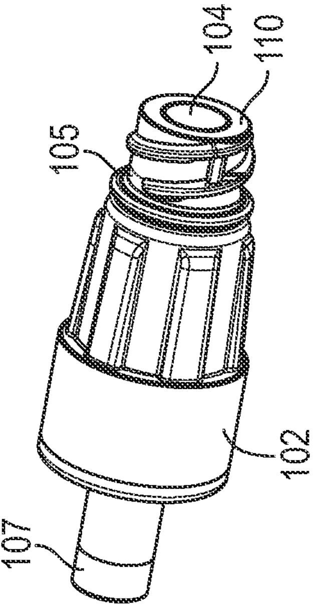

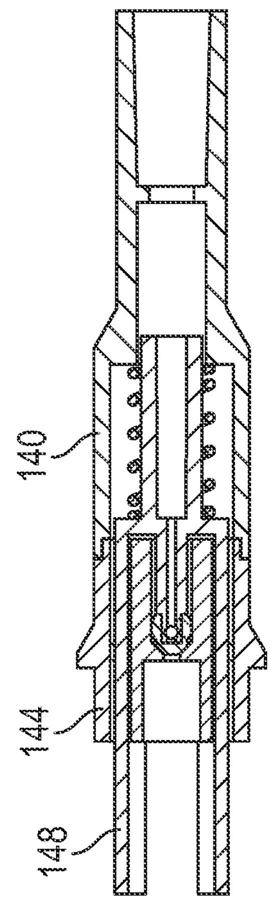
FIG. 7B
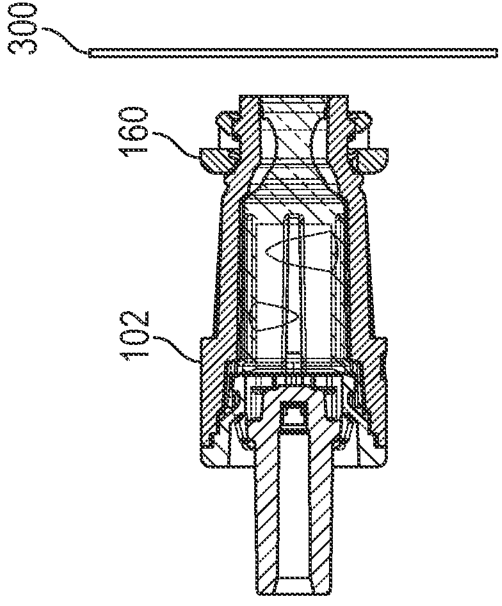

CONNECTOR COUPLING ASSEMBLY

CROSS-REFERENCE TO RELATED APPLICATION

This application claims the benefit of U.S. Provisional Patent Application No. 63/432,666 filed Dec. 14, 2022 entitled "Connector Coupling Assembly", which is incorporated by reference herein in its entirety.

FIELD OF THE INVENTION

The present disclosure generally relates to connectors, and, in particular, to connector couplings.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Often, tubing or catheters are coupled or secured to each other to allow fluid communication between various portions of tubing or catheters.

In some applications, such tubing or catheters may become dislodged due to improper securement and/or when the coupling is subject to forces greater than what the coupling is designed to withstand.

SUMMARY

One or more embodiments of the present disclosure are directed to a coupler including a first connector having a first end, a second end opposite the first end, and a valve extending from an area proximate the second end to an area proximate the first end, a second connector having a mating portion and a connecting portion opposite the mating portion, and a collar having a connecting end detachably coupled to the mating portion of the second connector and an engaging end disposed opposite the connecting end, the collar including a thread detachably coupled to the engaging end, the thread configured to couple to at least a portion of the first connector to detachably couple the first connector to the collar and the second connector such that the first connector, the collar, and the second connector form a fluid pathway. The first connector and the thread are configured to decouple from the collar while the collar remains coupled to the second connector when the first connector and the thread are coupled together.

In some embodiments, the first connector and the thread are configured to decouple from the collar in response to a pullout force exceeding a predetermined threshold force. The collar may be configured to decouple from the second connector in response to a compressive force, the compressive force being different than the pullout force. The pullout force may be a force applied to the first connector along a central axis of the first connector.

In some embodiments, the central axis extends at least along a length of the first connector. The central axis may extend through the first connector, the thread, the collar, and the second connector when the first connector is coupled to the collar via the thread and the collar is coupled to the second connector.

In some embodiments, the first connector is coupled to the thread and is configured to remain coupled to the collar when the pullout force does not exceed the predetermined threshold force.

In some embodiments, the collar includes a luer extending from at least the engaging end to at least the connecting end and the valve is configured to receive the luer when the first connector is coupled to the collar. The luer may be at least partially disposed within the second connector when the collar is coupled to the second connector. A portion of the luer may be disposed within the mating portion of the second connector when the collar is coupled to the second connector.

In some embodiments, the second connector includes a body disposed within the second connector, the body having a tube at least partially extending into the connecting portion and a pin at least partially extending into the mating portion. The body may include an extending arm extending from the body away from the tube, the extending arms configured to extend at least partially into the collar when the collar is coupled to the second connector.

In some embodiments, the thread is threaded to threadably engage with the second end of the first connector.

In some embodiments, the collar includes an engaging arm detachably coupling the collar to the thread, the engaging arms configured to release the thread when the thread is coupled to the first connector and a pullout force is applied to the first connector that exceeds a predetermined threshold force.

In some embodiments, the collar includes a connecting arm detachably coupling the collar to the mating portion of the second connector, the connecting arms configured to decouple from the mating portion.

In some embodiments, the coupler has a first configuration and in the first configuration the first connector is decoupled from the collar, the thread is detachably coupled to the collar, and the collar is coupled to the second connector.

In some embodiments, the coupler has a second configuration and in the second configuration the first connector is coupled to the thread, the thread is coupled to the collar, and the collar is coupled to the second connector.

In some embodiments, the coupler has a third configuration and in the third configuration the first connector is coupled to the thread, the first connector and the thread are disconnected from the collar, and the collar is coupled to the second connector.

In some embodiments, the coupler has a fourth configuration and in the fourth configuration the first connector is coupled to the thread, the first connector and the thread are disconnected from the collar, and the collar is decoupled from the second connector.

In some embodiments, when the first connector couples to the collar, the thread engages with the second end of the first connector to secure the first connector to the collar.

In some embodiments, the first connector is coupled to a first portion of tubing at the first end and the second connector is coupled to a second portion of tubing at the connecting portion.

In some embodiments, the mating portion has a maximum diameter greater than a maximum diameter of the connecting portion.

One or more embodiments of the present disclosure are directed to a coupler including a first connector having a first end, a second end opposite the first end, and a valve disposed within the first connector, the first end including threads, a second connector having a mating portion, a connecting portion opposite the mating portion, and a body at least partially disposed between the mating portion and the connecting portion, and a collar having at least one connecting arm at a connecting end, and at least one engaging arm at an engaging end, the connecting portion being disposed opposite the engaging end, the collar having a thread disposed at the engaging end. The collar is configured to couple the first connector to the second connector to form a fluid pathway. The first connector and the thread configured to decouple from the collar and the second connector, when the first connector is coupled to the thread, in response to a pullout force exceeding a predetermined threshold force.

One or more embodiments of the present disclosure are directed to a coupler including a first connector having a first end, a second end opposite the first end, and a valve disposed within the first connector, the first end including threads, a second connector having a mating portion, a connecting portion opposite the mating portion, and a body at least partially disposed between the mating portion and the connecting portion the body having a valve configured to fluidly seal the second connector and configured to axially move relative to the mating portion and the connecting portion, and a collar having a luer disposed within, at least one connecting arm at a connecting end, and at least one engaging arm at an engaging end, the connecting portion being disposed opposite the engaging end, the collar having a thread disposed at the engaging end, the thread configured to releasably couple to the at least one engaging arm. The thread is configured to mate with the threads of the first end. The collar is configured to couple the first connector to the second connector to form a fluid pathway such that a first portion of the luer is disposed within the first connector and a second portion of the luer opposite the first portion is disposed within the second connector. The first connector and the thread configured to decouple from the collar and the second connector, when the first connector is coupled to the thread, in response to a pullout force exceeding a predetermined threshold force. A central axis extends through the first connector, the thread, the collar, and the second connector when the collar is coupled to the first connector and the second connector. When the first connector is coupled to the thread and the first connector and the thread are decoupled from the collar, the collar is configured to decouple form the second connector in response to a compressive force, the compressive force being different than the pullout force.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 2A is a top perspective view of the coupler assembly of FIG. 1A showing the first connector decoupled from the thread, the collar, the second connector, in accordance with some embodiments of the present disclosure.

FIG. 7B is a cross sectional side view of the coupler assembly of FIG. 7A.

DETAILED DESCRIPTION

Figure 1A:
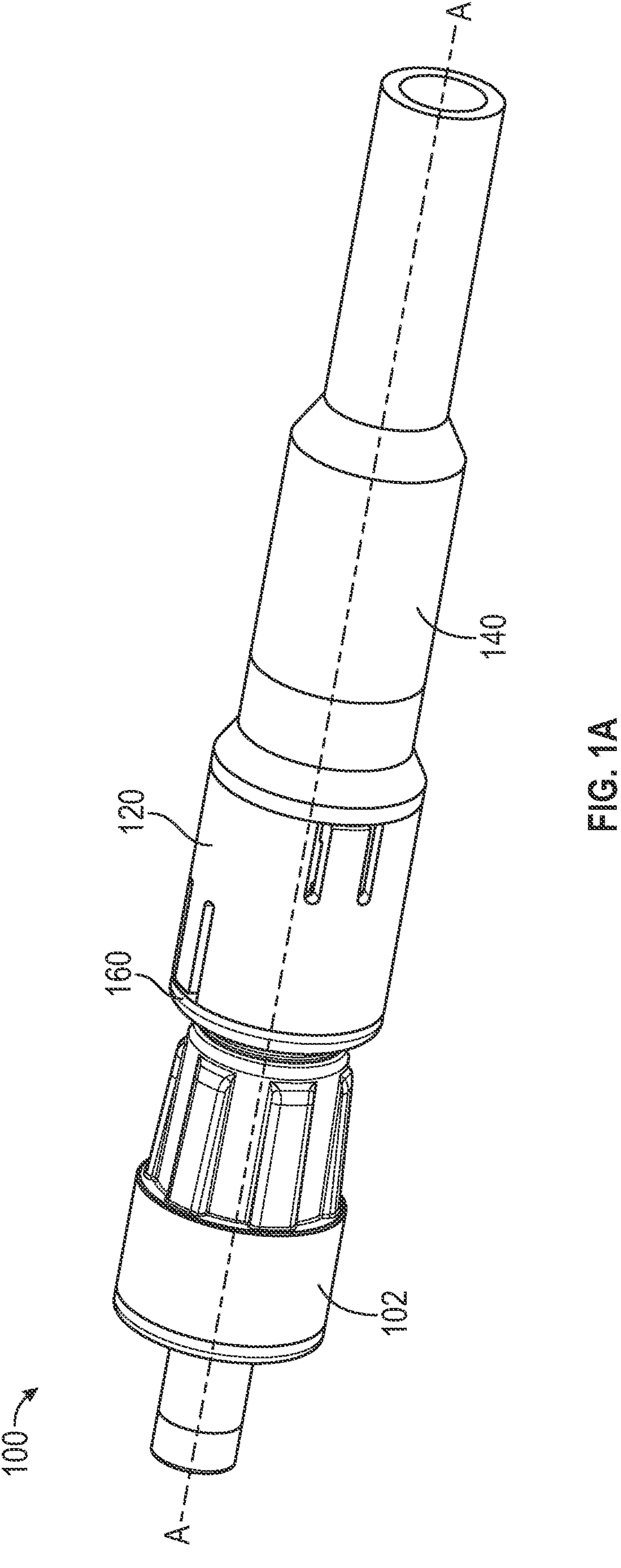
FIG. 1A is a top perspective view of a coupler assembly having a first connector, a thread, a collar, and a second connector, in accordance with various aspects of the present disclosure.

The disclosed coupler assembly includes a first connector, a thread, a collar, and a second connector. The collar is configured to couple the first connector to the second connector. In some embodiments, the collar includes a thread that is configured to couple to the first connector. The thread may be detachably coupled to the collar. The coupler assembly may have a first configuration, a second configuration, a third configuration, and a fourth configuration. In the first configuration, the thread is coupled to the collar, which is coupled to the second connector, and the first connector is decoupled from the thread, the collar, and the second connector. In the second configuration, the first connector is coupled to the thread and the collar, which is also coupled to the second connector. In the third configuration, the first connector is coupled to the thread, which is decoupled from the collar, which is coupled to the second connector. In the fourth configuration, the first connector is coupled to the thread, which is decoupled from the collar, which is decoupled to the second connector.

The coupler assembly may be configured to couple a first portion of tubing to a second portion of tubing. For example, the first portion of tubing may be coupled to the first connector and the second portion of tubing may be coupled to the second connector. The first portion of tubing and/or the second portion of tubing may also couple to a patient or fluid source. In some embodiments, the coupler assembly allows for the flow of fluid from the first portion of tubing to the second portion of tubing. For example, the collar and the thread may couple the first connector to the second connector such that a fluid pathway is formed through the first connector and the second connector to allow the flow of fluid from the first portion of tubing through the first connector and the second connector to the second portion of tubing. The fluid pathway may allow for the flow of fluid from the second portion of tubing through the second connector and the first connector to the first portion of tubing.

In some embodiments, the collar includes a thread that is configured to couple the collar to the first connector. The collar may be detachably coupled to the thread such that when the thread and the collar are couple to the first connector, the collar is configured to detach (e.g., decouple) from the thread and the first connector. The collar is configured to allow the first connector to decouple from the second connector. For example, the collar may couple the first connector to the second connector and may be configured to allow the first connector to decouple from the collar and the second connector due to a disconnection event. The collar may allow for one way connection of the first connector to the collar. The collar may be discarded or replaced with a new sterile connector to prevent infection or contamination that can occur if the connector is re-used (e.g., coupled again to the collar and the second connector).

In some embodiments, the first connector is configured to decouple based on a force that exceeds a predetermined threshold force. When a force is applied to the first connector, such as a pullout force, that exceeds the predetermined threshold force, the first connector may decouple from the collar and the second connector. In some embodiments, the collar is coupled to the first connector via the thread such that when the pullout force exceeds the predetermined threshold force the collar is decoupled from the thread and the first connector. This results in the thread remaining coupled to the first connecter. The pullout force may be a force that occurs along the longitudinal axis of the first connector. In some embodiments, the pullout force is caused by tugging or pulling on the first portion of tubing coupled to the first connector. Alternatively, the pullout out force applied to the first connector may be caused by tugging or pulling on the second connector and/or the second portion of tubing coupled to the second connector.

In some embodiments, once the first connector and the thread are decoupled from the collar and the second connector, the first connector and the thread are configured to not be re-coupled to the collar. For example, once the first connector, which is coupled to the thread, decouple from the collar, the first connector may not be able to re-couple to the collar via the thread to prevent attachment of the first connector and the thread to the collar and second connector after a disconnection event. The collar may include engaging arms that are configured to couple to and secure the thread to the collar. The engaging arms may secure the thread to the collar and may allow for decoupling of the thread from the collar in response to a disconnection event. In some embodiments, the thread couples the collar to the first connector and decouples from the collar while remaining coupled to the first connector. For example, upon the first connector decoupling from the collar, and the second connector, the thread remains attached to the first connector.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for case of understanding. Reference numbers may have letter suffixes appended to indicate separate instances of a common element while being referred to generically by the same number without a suffix letter.

While the following description is directed to the connection of medical fittings for the administration of medical fluid using the disclosed coupler, it is to be understood that this description is only an example of usage and does not limit the scope of the claims. Various aspects of the disclosed coupler may be used in any application where it is desirable to secure the connection of various tubing and fittings.

The disclosed coupler assembly overcomes several challenges discovered with respect to certain conventional couplers. One challenge with certain conventional couplers is that certain conventional couplers may be improperly secured. Further, during use, certain conventional couplers may be designed to release or dislodge in response to relatively low pullout forces. For example, certain conventional couplers may release in response to pullout forces experienced during patients rolling over in bed, patients catching tubing or lines on bed rails, moving patients to a different bed, fidgeting by pediatric patients, and/or disoriented adult patients pulling out their lines. Indeed, the Association for Vascular Access (AVA) Annual Scientific Meeting in 2017 reported a 10% dislodgement rate for 1,000 patients fitted with peripheral IV catheters, translating to approximately 33 million dislodgements per year in the U.S. alone. Because the accidental or unintentional dislodgement of tubing, catheters, or fittings may interrupt the administration of medical fluids, the use of certain conventional couplers is undesirable.

Further, conventional couplers may allow for re-attachment of a connector to a second connector or another connector after a disconnection event. Re-attachment after a disconnection event can lead to infection. For example, conventional couplers may include two connectors (e.g., second connectors, connectors, couplers, tubes, etc.)

coupled together to provide a fluid pathway from a fluid source to a patient. The two connectors of the conventional coupler may be de-coupled from each other due to a disconnection event and may result in on one or both of the connectors contacting the floor, another patient, another bed, or another individual which can result in contaminants (e.g., debris, bacteria, viruses, or other harmful elements) being disposed on the connector. Conventional couplers may allow the connectors to be re-coupled resulting in an increased risk of infection due to contaminants entering the fluid pathway.

Therefore, in accordance with the present disclosure, it is advantageous to provide couplers and coupler/connector assemblies as described herein that allows for improved securement of fittings or connectors. The disclosed couplers and coupler/connector assemblies are structured as described herein so as to permit the secure retention of the connectors, while preventing re-coupling of the connectors after a disconnection event.

Figure 1B:
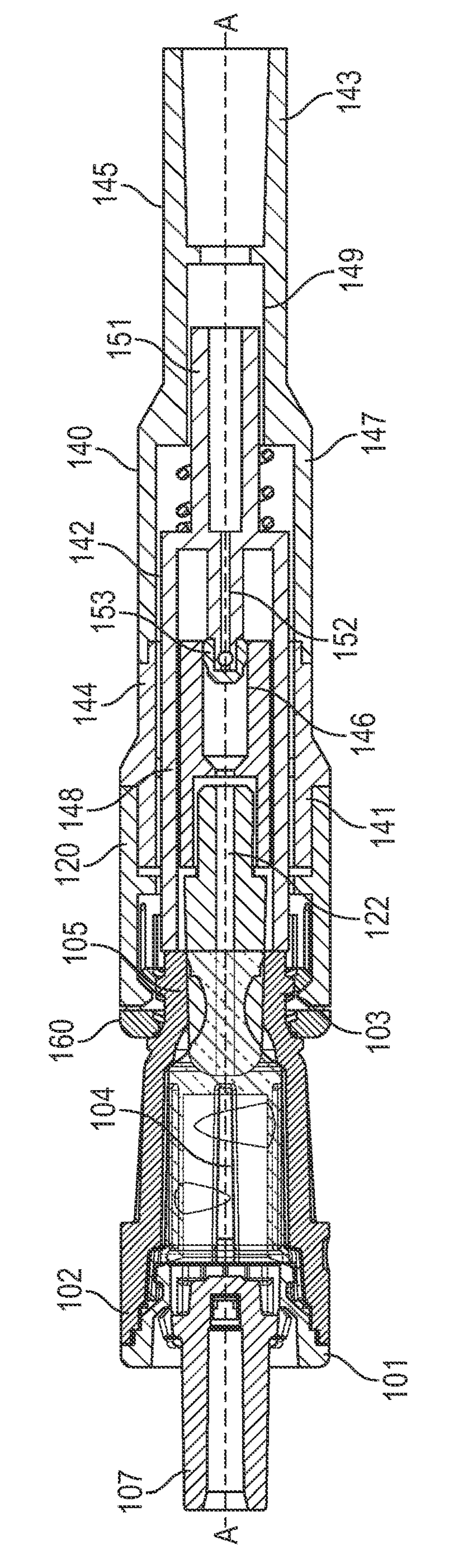
FIG. 1B is a cross sectional side view of the coupler assembly of FIG. 1A.
Figure 2B:
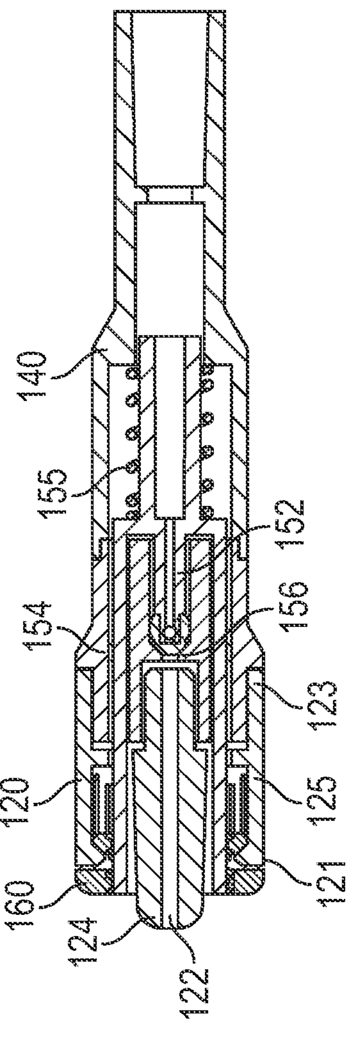
FIG. 2B is a cross sectional side view of the coupler assembly of FIG. 2A.
Figure 2B:
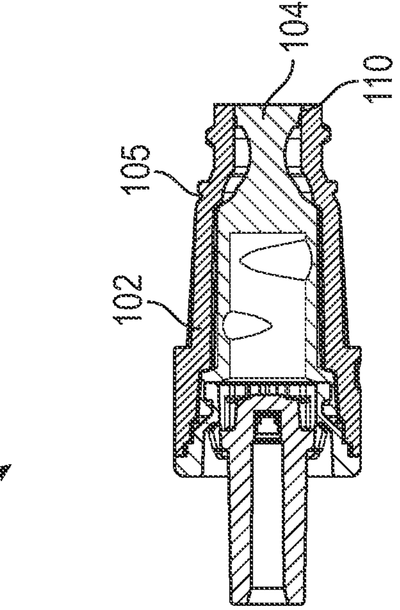

FIG. 1A is a top perspective view of a coupler assembly having a first connector, a thread, a collar, and a second connector, in accordance with various aspects of the present disclosure. FIG. 1B is a cross sectional side view of the coupler assembly of FIG. 1A. FIG. 2A is a top perspective view of the coupler assembly of FIG. 1A showing the first connector decoupled from the thread, the collar, the second connector, in accordance with some embodiments of the present disclosure. FIG. 2B is a cross sectional side view of the coupler assembly of FIG. 2A.

With reference to FIGS. 1A-1B, coupler assembly 100 allows the flow of a fluid, such as a medical fluid, from a fluid source to a patient by releasably coupling a portion of tubing or line with another portion of tubing or line in fluid communication. Coupler assembly 100 may include first connector 102, thread 160, collar 120, and second connector 140. Collar 120 may be configured to couple first connector 102 to second connector 140. Collar 120 may include thread 160 and be configured to couple to first connector 102 via thread 160. In the depicted example, portions of tubing can be terminated with connectors/second connectors, such as first connector 102 and/or second connector 140. In some embodiments, coupler assembly 100 includes central axis A-A and first connector 102, thread 160, collar 120, and second connector 140 are coupled in series along central axis A-A. Central axis A-A may extend longitudinally along the length of first connector 102, collar 120, and second connector 140. First connector 102 and/or second connector 140 may allow for the connection and/or disconnection of tubing to allow for selective fluid communication therebetween. In some embodiments, coupling of first connector 102, thread 160, collar 120, and second connector 140 creates a fluid pathway between a portion of first tubing coupled to first connector 102 and a portion of second tubing coupled to second connector 140.

In some embodiments, first connector 102 is coupled to second connector 140 via collar 120 and thread 160. Collar 120 may be configured to detachably couple first connector 102 to second connector 140 such that a portion of collar 120 is disposed within first connector 102 and that a portion of collar 120 is disposed within second connector 140. For example, when collar 120 couples to first connector 102, via thread 160, and second connector 140, a portion of collar 120 may be at least partially disposed within first connector 102 and another portion of collar 120 may be at least partially disposed within second connector 140. Collar 120 may be configured to allow for one way connection of first connector 102 to collar 120 via thread 160. Collar 120 may be configured to prevent re-coupling of first connector 102 and thread 160 to collar 120 once first connector 102 and thread 160 are decoupled from collar 120. Collar 120 may be configured to allow one way connection of first connector 102 to collar 120 via thread 160.

In some embodiments, first connector 102 is coupled to a first portion of tubing to allow the first portion of tubing to be connected and/or disconnected with second connector 140. First connector 102 may include first end 101 and second end 103. First end 101 may be coupled to tubing (e.g., a first portion of tubing) and second end 103 may be configured to couple to collar 120. Second 103 may be configured to couple to collar 120 via thread 160. In some embodiments, a portion of tubing can be coupled with, or engage with first end 101 of first connector 102. First connector 102, via first end 101, may be in fluid communication with the tubing to allow fluid to pass through first connector 102. In some embodiments, first end 101 can have a flat surface to allow for clinicians to easily clean and disinfect first end 101. First end 101 may be in fluid connection with second end 103. First end 101 and second end 103 may be disposed along the longitudinal length of first connector 102. For example, first end 101 and second 103 may be disposed along central axis A-A. First end 101 and/or second end 103 may include an opening to allow first end 101 and/or second end 103 to be in fluid communication with one or more elements (e.g., tubing, connectors, second connectors, collars, attachments, etc.). For example, first end 101 may be coupled to a tube and second end 103 may include opening 110 to allow for fluid communication through first connector 102. In some embodiments, first connector 102 includes a portion of collar 120, which is at least partially disposed within opening 110.

In some embodiments, fluid can exit or flow through first connector 102 via second end 103 disposed opposite to first end 101. The flow path through first connector 102 can have a straight fluid pathway to make flushing easier and to reduce the risk of hemolysis. Optionally, first connector 102 can include features (e.g., raised features, gripping features) disposed on the outer surface of first connector 102 to allow a clinician to more easily handle or manipulate first connector 102. Some embodiments of first connector 102 may provide connectors that are compatible with connectors of other portions of fluid delivery systems. First connector 102 may be substantially cylindrically shaped.

In some embodiments, first connector 102 includes valve 104, coupling portion 105, and tubing portion 107. First connector 102 may be a needleless connector. Valve 104 may be disposed within first connector 102 and may be configured to control the flow of fluid within first connector 102. Valve 104 may extend from a portion proximate first end 101 to a portion proximate second end 103. In some embodiments, valve 104 extends from tubing portion 107 to coupling portion 105. Valve 104 may terminate at opening 110. In some embodiments, valve 104 is configured to receive a portion of collar 120 (e.g., luer 124). Valve 104 may be comprised of a flexible material, such as an elastomer, to receive a portion of collar 120 to create a fluid pathway between first connector 102 and collar 120. Valve 104 may create a tight seal around a portion of collar 120 (e.g., luer 124) when first connector 102 is coupled to collar 120. In some embodiments, tubing portion 107 is configured to couple to a portion of tubing. Tubing portion 107 may be in fluid communication with valve 104 to allow for fluid to flow from a portion of tubing coupled to tubing portion 107 through valve 104 and out of opening 110.

Coupling portion 105 may be disposed proximate first end 101. Coupling portion 105 may be configured to couple with thread 160 to detachably couple first connector 102 to collar 120. In some embodiments, coupling portion 105 is threaded to allow for coupling portion 105 to threadably engage with thread 160 of collar 120. In some embodiments, at least a portion of valve 104 is disposed within coupling portion 105.

Similar to first connector 102, a second portion of tubing can be terminated by second connector 140 to allow the second portion of tubing to be connected and/or disconnected from collar 120 via second connector 140. Second connector 140 may include first end 141 and second end 143 disposed opposite first end 141. First end 141 may include mating portion 144 and second end 143 may include connecting portion 145, which may be disposed opposite mating portion 144. In some embodiments, a portion of tubing is coupled with, or engage with connecting portion 145 of second connector 140. In some embodiments, connecting portion 145 includes a threaded connection to facilitate coupling with tubing.

In some embodiments, mating portion 144 includes features (e.g., threads) that allow for second connector 140 to mate with collar 120. Mating portion 144 may fit together or otherwise engage with collar 120 to allow fluid communication between collar 120 and second connector 140 and the portions of tubing coupled thereto when second connector 140 is coupled to collar 120. In some embodiments, first connector 102 and second connector 140 are coupled and decoupled via collar 120 to permit fluid communication as desired. First connector 102 may be detachably coupled with second connector 140 via collar 120 to provide needle free connections. Advantageously, first connector 102 may pair with second connector 140 via collar 120 and thread 160 to form a leak-free closed system, allowing the delivery of various drugs or fluids.

In some embodiments, second connector 140 includes housing 147. Housing 147 may be disposed between first end 141 (e.g., mating portion 144) and second end 143 (e.g., connecting portion 145). In some embodiments, housing 147 is disposed between mating portion 144 and connecting portion 145. In some embodiments, mating portion 144 is coupled to housing 147, which is coupled to connecting portion 145. Housing 147 may have a maximum diameter greater than the maximum diameter of connecting portion 145. In some embodiments, mating portion 144, housing 147, and connecting portion 145 form a unitary structure. Mating portion 144 may be disposed proximate first end 141. Mating portion 144 may include threads configured to couple second connector 140 to collar 120. Alternatively, mating portion 144 may include fasteners, adhesives, magnets, or other components to configured to couple second connector 140 to collar 120. In some embodiments, collar 120 may be secured to second connector 140 by engaging with mating portion 144. Connecting portion 145 may include channel 149 extending within connecting portion 145. Channel 149 may extend through connecting portion 145 along central axis A-A. Channel 149 may allow connecting portion 145 and second connector 140 to be in fluid communication with a portion of tubing coupled to connecting portion 145.

In some embodiments, second connector 140 includes body 142, which includes extending arms 148, pin 152 and tube 151. Body 142 may be disposed within second connector 140 (e.g., within housing 147). In some embodiments, at least a portion of body 142 is disposed within channel 149 of connecting portion 145. For example, a least a portion of body 142 may be extend into channel 149. In some embodiments, tube 151 of body 142 at last partially extends into channel 149. Tube 151 may be hollow to allow channel 149 to be in fluid communication with tube 151. In some embodiments, body 142 includes pin 152 in fluid communication with tube 151. Pin 152 may extend from tube 151 and sealing valve 153 may be disposed at an end of pin 152. In some embodiments, sealing valve 153 is disposed at an end of pin 152 opposite tube 151. Scaling valve 153 may be configured to control the flow of fluid within pin 152 and tube 151. For example, sealing valve 153 may be configured to be in an open position and a closed position. In the open position, sealing valve 153 allows for the flow of fluid out of second connector 140. In the closed position, scaling valve 153 blocks or prevents flow of fluid out of second connector 140.

In some embodiments, in the open configuration, valve 153 is configured to allow fluid to flow from first end 141 to second end 143, or vice versa. In the closed configuration, valve 153 may be configured to block or prevent the flow of fluid in or out of first end 141 (e.g., mating portion 144) and/or second end 143 (e.g., connecting portion 145). In some embodiments, valve 153 is in the open configuration when first connector 102 is coupled to second connector 140 via collar 120. valve 153 may be in the closed position upon disconnecting or decoupling of first connector 102 from second connector 140 and/or collar 120.

In some embodiments, extending arms 148 extend away from tube 151. Extending arms 148 may be configured to extend from an area proximate tube 151 through mating portion 144 and out of second connector 102. For example, mating portion 144 may include grooves 154 and extending arms 148 may be disposed within grooves 154. In some embodiments, extending arms 148 extend through grooves 154. Grooves 154 may be sized and shaped to channel extending arms 148. Extending arms 148 may be configured to extend through collar 120 when collar 120 is coupled to second connector 140. In some embodiments, extending arms 148 extend through collar 120 and thread 160 when collar 120 and thread 160 are coupled to second connector 140.

Mating portion 144 may also include channel 146 and opening 156. Opening 156 may be disposed at or proximate an end of channel 146. Channel 146 may be disposed opposite opening 156. Channel 146 may be configured to receive pin 152. Channel 146 may be sized and shaped to receive pin 152 such that pin 152 is at least partially disposed within channel 146. In some embodiments, sealing valve 153 is disposed at end of pin 152 such that the sealing valve 153 is disposed within channel 146. Channel 146 may be in fluid communication with opening 156. In some embodiments, channel 149 is in fluid communication with tube 151 which is fluid communication with pin 152, which includes valve 153. Pin 152 may be in fluid communication with channel 146, which is in fluid communication with opening 156. This allows a portion of tubing coupled to connecting portion 145 to be in fluid communication with opening 156.

In some embodiments, a portion of collar 120 is disposed within opening 156 when collar 120 is coupled to second connector 140. A portion of collar 120 (e.g., luer 124) may be disposed within opening 156 when collar 120 is coupled to second connector 140 to allow second connector 140 to be in fluid communication with collar 120. This allows fluid to flow through channel 146 to opening 156 and through collar 120 (e.g., via luer 124). In some embodiments, opening 156 is sized and shaped to securely receive a portion of collar 120.

In some embodiments, collar 120 is configured to couple first connector 102 to second connector 140. Collar 120 may include thread 160, which is detachably coupled to collar 120. Collar 120 includes first end 121 (engaging end) and second end 123 (connecting end). In some embodiments, when collar 120 couples first connector 102 to second connector 140, central axis A-A extends through first end 121 and second end 123. When collar 120 couples first connector 102 to second connector 140, first end 121 may be proximate first connector 102 and second end 123 may be proximate to second connector 140. Collar 120 may include luer 124 extending through collar 120. Luer 124 may extend from an area proximate first end 121 to an area proximate second end 123. Luer 124 may include luer channel 122 disposed within luer 124 and extending through luer 124. In some embodiments, luer channel 122 extends from an area proximate first end 121 to an area proximate second end 123.

First end 121 of collar 120 may be configured to couple to first connector 102 and second end 123 of collar 120 may be configured to couple to second connector 140. In some embodiments, first end 121 of collar 120 couples to second end 103 of first connector 102 and second end 123 of collar 120 couples to first end 141 (e.g., mating portion 144) of second connector 140. Second end 123 of collar 120 may be configured to couple to mating portion 144 of second connector 140. In some embodiments, first end 121 includes threads disposed on an interior surface of collar 120, which are configured to mate with threads disposed on coupling portion 105 of first connector 102 to secure collar 120 to first connector 102.

Collar 120 may include engaging arms 125. Engaging arms 125 may be cantilevers that are configured to allow collar 120 to engage and disengage with thread 160. Collar 120 may include more than one engaging arm 125, such as two, three, four, five, or greater than five engaging arms. In some embodiments, engaging arms 125 are configured to couple to thread 160. Engaging arms 125 may include protrusions 126 disposed proximate first end 121 of collar 120. When thread 160 is coupled to collar 120, protrusions 126 may be disposed within notch 163. Engaging arms 125 may be configured to allow thread 160 to detachably couple to collar 120. In some embodiments, protrusions 126 may be friction fit into notch 163 to secure thread 160 to collar 120. In some embodiments, engaging arms 125 allow a portion of thread 160 (e.g., second end 164) to be friction fitted into collar 120 causing protrusions 126 of engaging arms 125 to be disposed within notch 163. In response to a pullout force exceeding a predetermined threshold force, the friction force between notch 163 and protrusion 126 may be overcome resulting in protrusions 126 and engaging arms 125 bending away from central axis A-A and allowing thread 160 to decouple from collar 120. In some embodiments, engaging arms 125 are biased towards central axis A-A such that when thread 160 is coupled to collar 120, thread 160 is friction fitted into collar 120 and protrusions 126 are disposed and secured with notch 163. Engaging arms 125 may be biased radially inwards towards central axis A-A to secure thread 160 to collar 120. When thread 160, and first connector 102, are decoupled from collar 120, engaging arms 125 may be radially deflected outwards and then may return to their initial position of being biased radially inwards towards central axis A-A. Engaging arms 125 being biased radially inwards prevents thread 160 from recoupling with collar 120. For example, once decoupled, thread 160 may not be recoupled to collar 120 without manually causing engaging arms 125 to radially deflect outwards. This prevents a user from easily recoupling thread 160 to collar 120.

In some embodiments, engaging arms 125 allow thread 160 to decouple from collar 120 when an axial force (e.g., pullout force) that is greater than a predetermined threshold force is applied to thread 160. In some embodiments, when collar 120 is coupled to first connector via thread 160 and second connector 140, engaging arms 125 are configured to allow thread 160 to decouple from collar 120 and remain coupled to first connector 102, thereby resulting in collar 120 and second connector decoupling from thread 160 and first connector 102.

Figure 3:
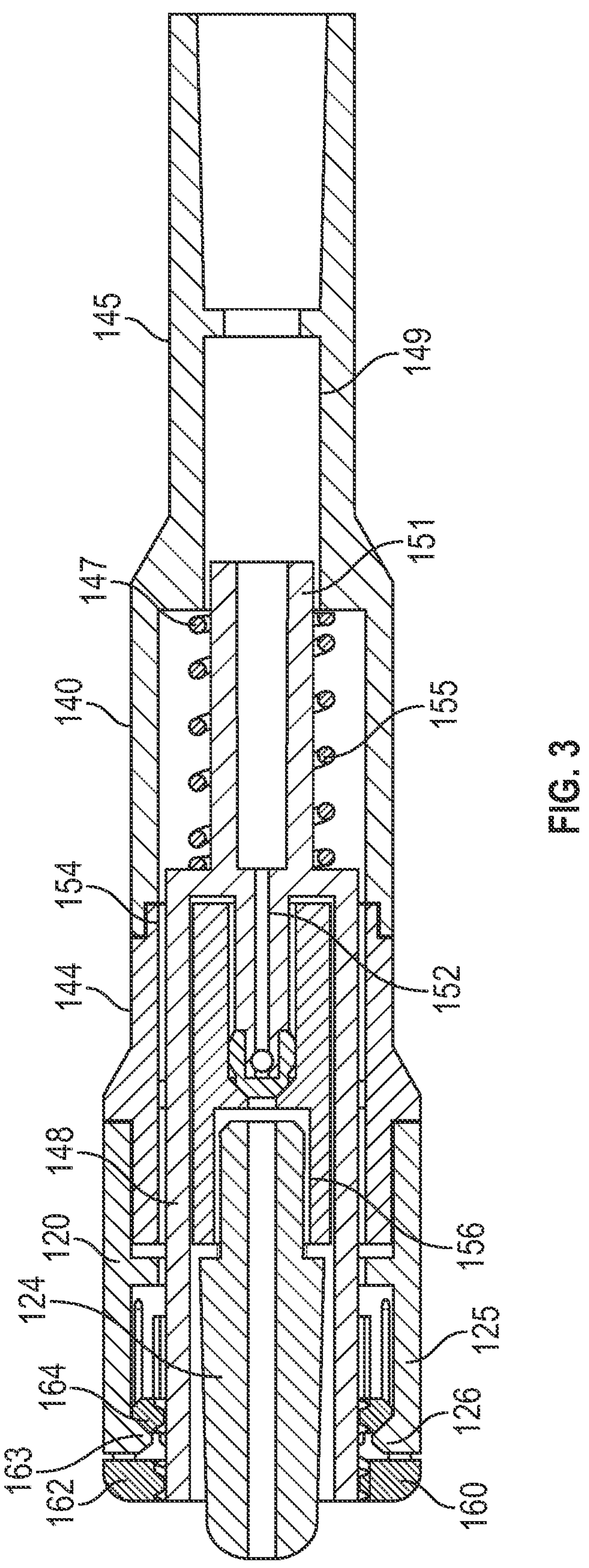
FIG. 3 is a cross sectional view of the thread coupled to the second connector of the coupler assembly of FIG. 1A, in accordance with some embodiments of the present disclosure.

FIG. 3 is a cross sectional view of the thread coupled to the second connector of the coupler assembly of FIG. 1A, in accordance with some embodiments of the present disclosure.

In some embodiments, collar 120 includes thread 160, which is configured to detachably couple to collar 120. Thread 160 may include first end 162 and second end 164. Thread 160 may be threaded throughout the length of thread 160. For example, an interior surface of thread 160 may be threaded. In some embodiments, the interior surface of thread 160 is threaded to mate with coupling portion 105 of first connector 102.

Thread 160 may include notch 163 disposed between first end 162 and second end 164. Notch 163 may be configured to receive a portion of engaging arms 125 (e.g., protrusion 126) to secure thread 160 to engaging arms 125 and collar 120. In some embodiments, first end 162 has a maximum diameter greater than second end 164. Second end 164 may be at least partially disposed within collar 120. In some embodiments, second end 164 is partially disposed within collar 120 proximate first end 121 and first end 162 of thread 160 abuts first end 121. Thread 160 may be configured to mate with first connector 102 to couple collar 120 to first connector 102. In some embodiments, collar 120 is coupled to second connector 140 and thread 160 is coupled to collar 120 and configured to mate with first connector 102 to couple collar 120 and second connector 140 to first connector 102. Thread 160 may be configured to decouple from collar 120 when thread 160 is coupled to or mated with first connector 102 and first connector 102 is decoupled from collar 120 due to a pullout force exceeding a predetermined threshold force. For example, engaging arms 125 may be configured to allow thread 160 to decouple from collar 120 when thread 160 is coupled to first connector 102 and a pullout force exceeding a predetermined threshold force is applied to thread 160 via first connector 102.

Referring to FIGS. 1A-1B, when first connector 102 is coupled to second connector 140 via collar 120 and thread 160, valve 104 of first connector 102 is proximate to or receives collar 120. When first connector 102 is coupled to second connector 140 via collar 120, luer 124 may be at least partially disposed within first connector 102 (e.g., valve 104) and second connector 140 such first connector 102 is in fluid communication with second connector 140 via collar 120. In some embodiments, when first connector 102 is coupled to second connector 140 via collar 120, a portion of first connector 102 may abut second connector 140. For example, second end 103 may be proximate to or abut extending arms 148 when first connector 102 is coupled to second connector 140 via collar 120. In some embodiments, when first connector 102 is coupled to second connector 140 via collar 120, collar 120 is disposed between a portion proximate second end 103 and first end 141.

In some embodiments, second connector 140 is coupled to tubing that is in fluid communication with connecting portion 145 to allow the tubing to receive fluid flow passing through second connector 140. Second connector 140 can receive fluid flow from first end 141 (e.g., mating portion 144) disposed opposite to second end 143 (e.g., connecting portion 145) or vice versa. In some embodiments, second connector 140 includes a no-drip feature to prevent leaks or surface contamination. Second connector 140 may further include a luer lock to prevent accidental discharges.

Similarly, first connector 102 can include a sealing valve (e.g., valve 104) to allow for flow to pass therethrough when first connector 102 is coupled to collar 120 and can prevent or restrict flow when connector is decoupled from collar 120. First connector 102 may include a sealing valve to seal the flow path between first end 101 and second end 103 when first connector 102 is decoupled from collar 120. Further, the sealing valve may be in an open position when first connector 102 is coupled to collar 120, allowing flow into first connector 102 and between first end 101 and second end 103. Some embodiments provide that portions of the sealing valve can be formed from silicone.

Referring to FIGS. 2A-2B, coupler assembly 100 may be configured to be in a first configuration. In the first configuration, collar 120, including thread 160, may be coupled to second connector 140 and first connector 102 may be decoupled or disconnected from collar 120 and second connector 140. In some embodiments, coupler assembly 100 is shipped or transported in the first configuration. Shipping or transporting coupler assembly 100 in the first configuration may prevent inadvertent compression of valve 104 and/or valve 153. For example, when first connector 102 is coupled to second connector 140 via collar 120, valve 104 of first connector 102 may be compressed (e.g., by luer 124 of collar 120). In the first configuration, first connector 102 is decoupled or disconnected from collar 120 resulting in valve 104 of first connector 102 not abutting or being proximate to collar 120 allowing valve 104 to be substantially decompressed. Accordingly, shipping or transporting coupler assembly 100 in the first configuration allows valve 104 to remain decompressed and thereby extends the life of valve 104.

In the first configuration, thread 160 and collar 120 are coupled to second connector 140 and first connector 102 is decoupled from thread 160 and collar 120. Thread 160 may be coupled to collar 120 and a portion of collar 120 (e.g., luer 124) may be disposed within opening 156 of second connector 140. For example, engaging arms 125 may be configured to secure thread 160 to collar 120 and collar 120 may be secured to second connector 140 by coupling to mating portion 144 and extending arms 148. In the first configuration, first connector 102 may be configured to couple to a first portion of tubing and second connector 140, with collar 120 and thread 160, may be configured to couple to a second portion of tubing.

Referring to FIGS. 1A-1B, coupler assembly 100 may be configured to be in a second configuration. Coupler assembly 100 may transition from the first configuration to the second configuration by coupling first connector 102 to thread 160 and collar 120. For example, coupling portion 105 of first connector 102 may threadably engage with the threads of thread 160 and valve 104 may receive luer 124 of collar 120. In the second configuration, thread 160 may be configured to mate with coupling portion 105 while still being coupled to collar 120 via engaging arms 125 thereby coupling first connector 102 to thread 160 and collar 120. First connector 102 may be coupled to thread 160 and collar 120 when coupler assembly 100 is in the second configuration such that valve 104 receives a portion of luer 124.

In the second configuration, first connector 102 may be coupled to thread 160 and collar 120, and collar 120 may be coupled to second connector 140. In some embodiments, in the second configuration, first connector 102, collar 120, and second connector 140 may be in fluid communication to allow fluid to flow from second end 143 of second connector 140 through collar 120 and first connector 102, and out of first end 101 or vice versa. In some embodiments, first connector 102 may be coupled a patient via a needler, catheter, and/or tubing and second connector 140 may be coupled to a fluid source. In the second configuration, fluid may flow from the fluid source through second connector 140, through collar 120 and first connector 102 to a patient or vice versa.

Figure 4A:
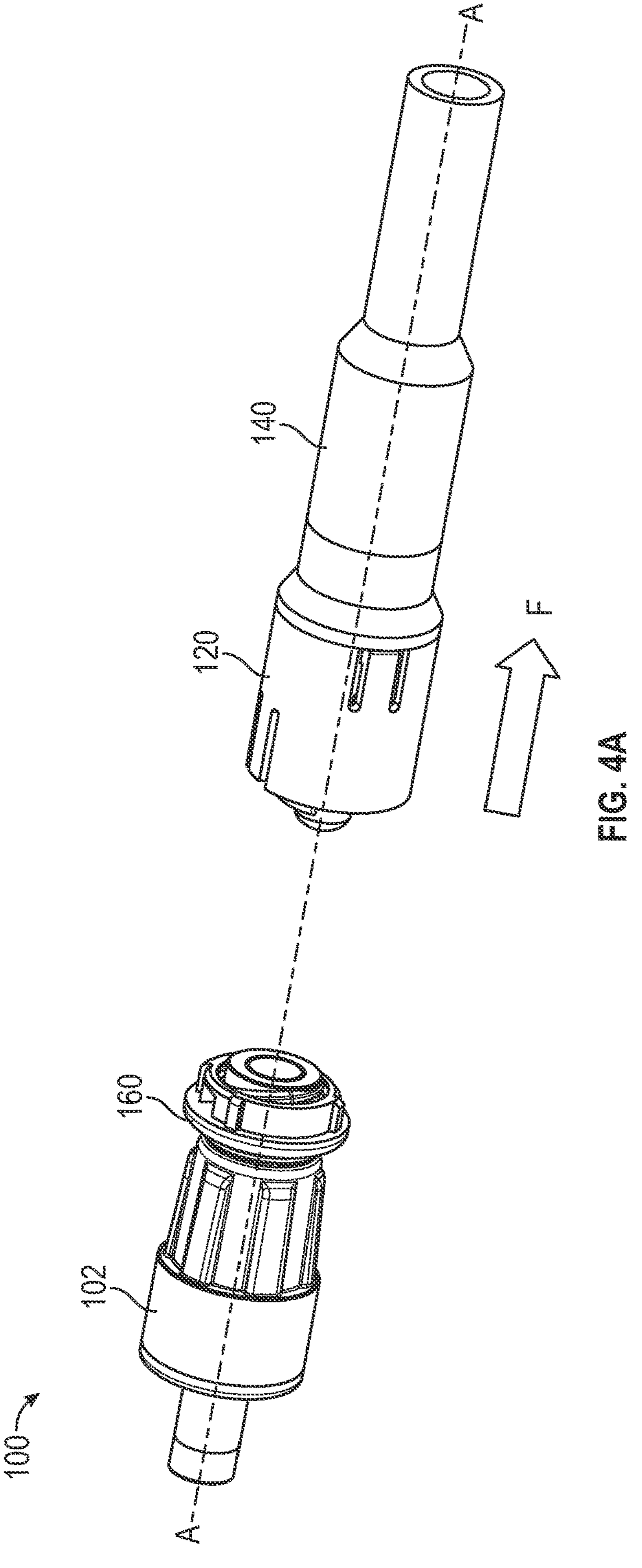
FIG. 4A is top perspective view of the coupler assembly of FIG. 1A showing the first connector coupled to the thread and decoupled from the collar and the second connector, in accordance with some embodiments of the present disclosure.
Figure 4B:
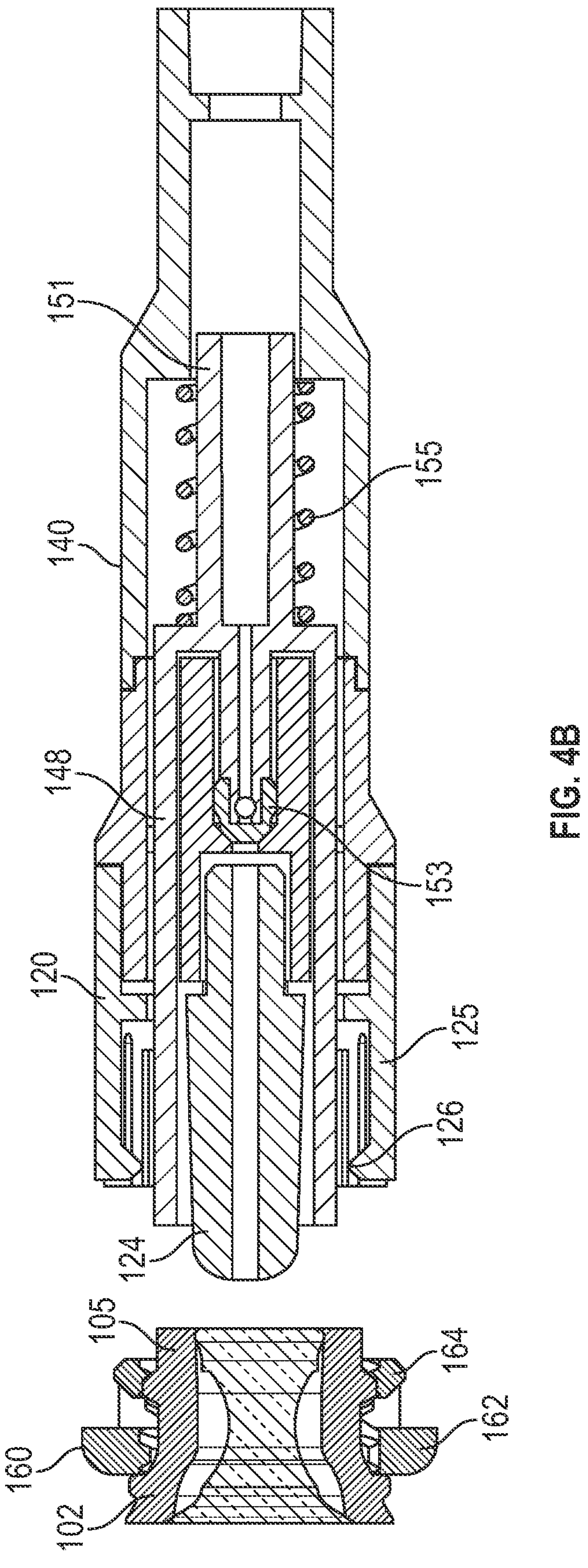
FIG. 4B is a zoomed in cross sectional side view of the coupler assembly of FIG. 4A.
Figure 5:
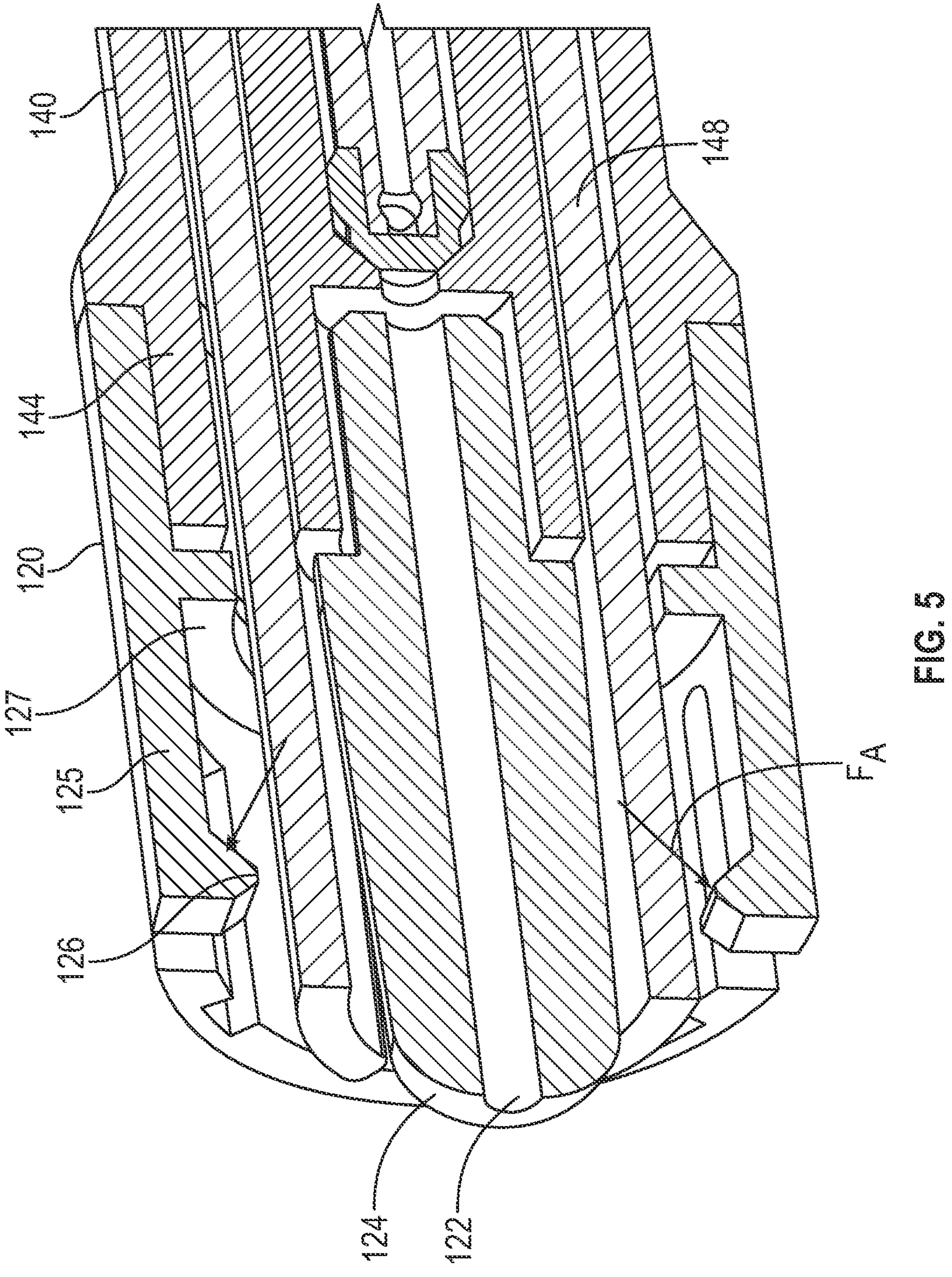
FIG. 5 is a zoomed in cross sectional side view of the collar and the second connector of the coupler assembly of FIG. 1A, in accordance with some embodiments of the present disclosure.

FIG. 4A is top perspective view of the coupler assembly of FIG. 1A showing the first connector coupled to the thread and decoupled from the collar and the second connector, in accordance with some embodiments of the present disclosure. FIG. 4B is a zoomed in cross sectional side view of the coupler assembly of FIG. 4A. FIG. 5 is a zoomed in cross sectional side view of the collar and the second connector of the coupler assembly of FIG. 1A, in accordance with some embodiments of the present disclosure.

Referring to FIGS. 4A-5, coupler assembly 100 may be configured to be in a third configuration. Coupler assembly 100 may transition from the second configuration to the third configuration by first connector 102 and thread 160 decoupling from collar 120 and second connector 140. For example, in the second configuration, first connector 102 may be coupled to thread 160 and collar 120. First connector 102 and thread 160 may decoupled from collar 120 resulting in coupler assembly 100 being in the third configuration. Thread 160 may be decoupled from collar 120 along with first connector 102 due to thread 160 being threadably engaged with coupling portion 105 of first connector 102.

In some embodiments, first connector 102, along with thread 160, is configured to decouple from collar 120 and second connector 140 in response to a pullout force (e.g., force F) exceeding a predetermined threshold force. For example, first connector 102 may decouple from collar 120 due to a disconnection event, which is caused by a pullout force (e.g., force F). For example, a pullout force (e.g., force F) may be applied to first connector 102, either by being directly applied to first connector 102 or indirectly applied to first connector 102, such as being applied to tubing coupled to first connector 102. The pullout force may cause first connector 102 along with thread 160 to move axially away from collar 120 and second connector 140 along central axis A-A thereby decoupling first connector 102 and thread 160 from collar 120 and second connector 140.

In some embodiments, first connector 102 and thread 160 are decoupled from collar 120, and thus second connector 140, when force F exceeds a predetermined threshold force. For example, if force F is less than the predetermined threshold force, first connector 102, along with thread 160, may not decouple from collar 120 and second connector 140. The predetermined threshold force prevents inadvertent or accidental decoupling based on minor forces or movements. The predetermined threshold force may be based on the coupling of engaging arms 125 to thread 160. For example, engaging arms 125 may be configured to releasably couple thread 160 to collar 120 and may allow thread 160 to decouple when force F exceeds the predetermined threshold force.

In some embodiments, the predetermined threshold force is approximately 5 pounds (lbs). The predetermined threshold force may be from approximately 1 lb to approximately 8 lbs, approximately 3 lbs to approximately 7 lbs, approximately 4 lbs to approximately 6 lbs, or greater than 8 lbs. For example, a patient may have a needle/catheter inserted into their skin and the needle/catheter may be coupled to first connector 102 or second connector 140. The patient may walk away from an infusion pump or accidental pull on a fluid line coupled to first connector 102 or second connector 140 and the force exceeds 5 lbs, first connector 102 and thread 160 may automatically release or decouple from collar 120, effectively closing the fluid pathway between first connector 102 and collar 120 and second connector 140, as described herein.

When first connector 102 and thread 160 decouple from collar 120 due to the disconnection event, collar 120 may remain secured and coupled to second connector 140. In some embodiments coupler assembly 100 is configured to be in a third configuration where first connector 102 is decoupled from collar 120 and collar 120 is secured and coupled to second connector 140. For example, first connector 102 and thread 160 may be decoupled from collar 120 and second connector 140 resulting in collar 120 remaining secured to second connector 140. First connector 102, including thread 160, being decoupled from collar 120 and second connector 140 results in first connector 102 and thread 160 being spaced apart from collar 120 and second connector 140.

First connector 102 may decouple from collar 120 in response to force F exceeding the predetermined threshold force. When force F exceeds the predetermined threshold force, second end 164 of thread 160 exerts an axial force (e.g., force FA) on protrusion 126, which may cause radial deflection of engaging arms 125. Radial deflection of engaging arms 125 due to force FA causes protrusion 126 to be removed from notch 163 in response to force F, thereby allowing thread 160, which is coupled to first connector 102, to axially move away from collar 120 and second connector 140 and decoupling first connector 102 from collar 120.

In some embodiments, when first connector 102 and thread 160 are decoupled from collar 120 and second connector 140, engaging arms 125 initially deflect outwards as thread 160 decouples from collar 120. Engaging arms 125 then return to their initial position of being biased radially inwards. When engaging arms 125 are returned to their initial position, thread 160 is prevented from being coupled to collar 120 thereby preventing first connector 102 from being coupled to collar 120. This prevents contamination of collar 120, second connector 140, and/or other components by first connector 102. For example, first connector 102 may be decoupled from second connector 140 and collar 120 based on a disconnection event (e.g., force F exceeding the predetermined threshold force). The disconnection event may cause first connector 102 and thread 160 to fall to the floor, contact another surface or patient, or otherwise be exposed to unclean or unsterile environments. Allowing recoupling of first connector 102 and thread 160 to second connector 140 after a disconnection event may result in contaminants (e.g., bacteria, debris, viruses, etc.) entering the fluid pathway between first connector 102, collar 120, and second connector 140, which may cause infection to the user (e.g., the patient). For example, during a disconnection event, collar 120 may include fluid and may contact the floor or other non-sterile environment causing the fluid within collar 120 to be contaminated. Recoupling collar 120 with first connector 102 may cause the contaminated fluid within 120 to flow through second connector 140 and to the patient and/or fluid source. In other words, allowing recoupling of first connector 102 to second connector 140 via collar 120 after a disconnection event may result in contaminants entering the bloodstream or other exposed areas of the patient resulting in sepsis.

In some embodiments, second connector 140 include biasing element 155. Biasing element 155 may be disposed around tube 151 of body 142. In some embodiments, biasing elements 155 is configured to bias body 142 away from second end 143 and/or connecting portion 145. Biasing element 155 may be a spring that is compressed towards second end 143 when first connector 102 is coupled to collar 120. When the first connector 102 is coupled to collar 120, the body 142 is configured to slide toward the second end 143 within the second connector 140. As the body 142 slides within the second connector 140 toward the second end 143 by contact with the coupling portion 105 and the force of coupling the first connector 102 with the second connector 140, the biasing element 155, or spring, is compressed toward the second end 143. In some embodiment, biasing element 155 is compressed due to the coupling of first connector 102 to collar 120, which is coupled to second connector 140. Upon decoupling of first connector 102 from collar 120, biasing element 155 may decompress (e.g., stretch out or expand) to push body 142 axially away from connecting portion 145.

Referring to FIG. 5, axially moving of body 142 away from connecting portion 145 results in body 142 moving towards mating portion 144 and thus pin 152 and valve 153 axially moving (along central axis A-A) towards opening 156. Pin 152 and valve 153 may axially move to abut the junction between opening 156 and channel 146, thereby sealing off the pathway between opening 156 and channel 146. This prevents fluid from flowing from second connector 140 through collar 120. In other words, upon decoupling of first connector 102 and thread 160 from collar 120 and second connector 140, pin 152 and valve 153 may axially move away from second end 143 due to biasing element 155 pushing body 142 away from second end 143 causing valve 153 to seal the fluid pathway between second connector 140 and collar 120.

Figure 6A:
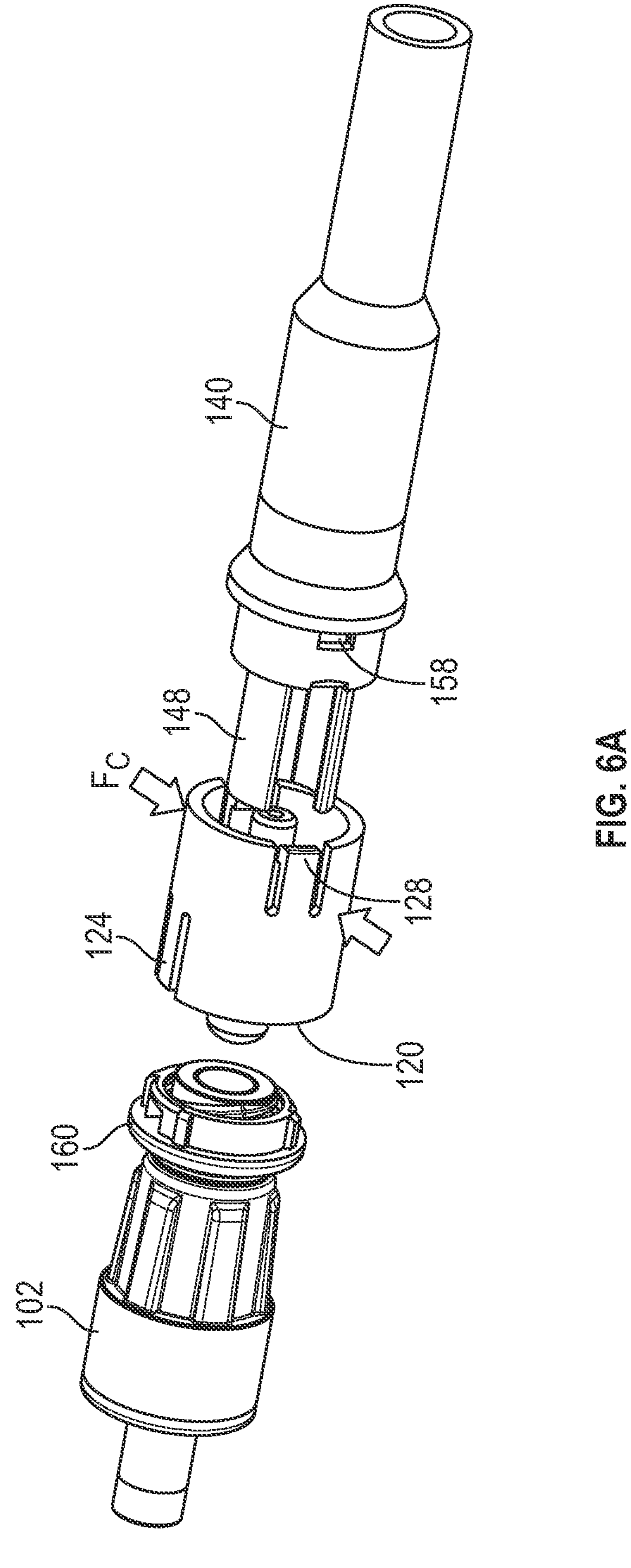
FIG. 6A is a top perspective view of the coupler assembly of FIG. 1A showing the thread coupled to the first connector and the collar decoupled from the second connector, in accordance with some embodiments of the present disclosure.
Figure 6B:
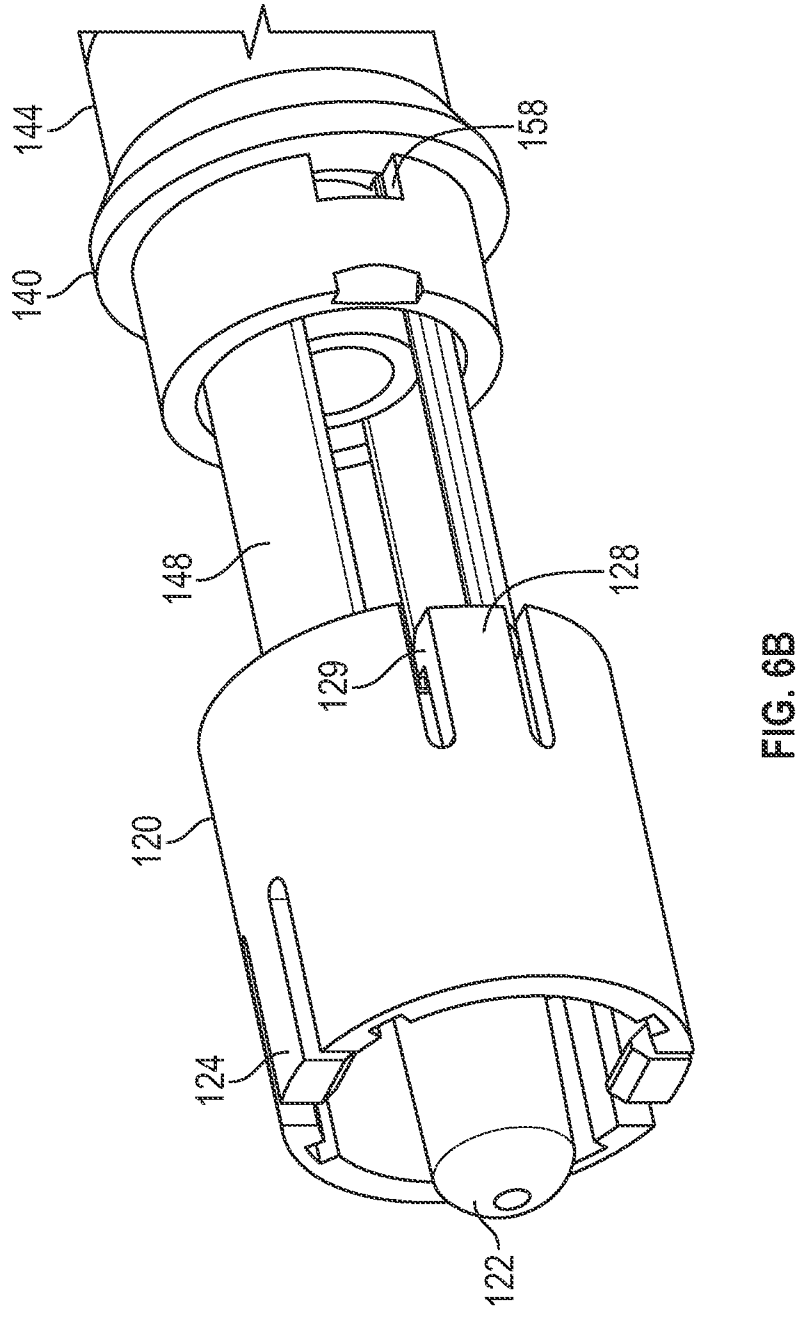
FIG. 6B is a zoomed in perspective view of the coupler assembly of FIG. 1A showing the collar decoupled from the second connector.

FIG. 6A is a top perspective view of the coupler assembly of FIG. 1A showing the thread coupled to the first connector and the collar decoupled from the second connector, in accordance with some embodiments of the present disclosure. FIG. 6B is a zoomed into perspective view of the coupler assembly of FIG. 1A showing the collar decoupled from the second connector.

Referring to FIGS. 6A-6B, coupler assembly 100 may be configured to be in a fourth configuration. Coupler assembly 100 may transition from the third configuration to the fourth configuration by decoupling collar 120 from second connector 140. Collar 120 may be decoupled from second connector 140 to discard and/or replace collars 120. Upon a disconnection event, first connector 102 and thread 160 are decoupled from collar 120 and are prevented from being recoupling to collar 120 and second connector 140. After the disconnection event, collar 120 may be disconnected from second connector 140. Collar 120 may be disconnected from second connector 140 may applying a compressive force (e.g., force Fc) to collar 120. For example, a compressive force (e.g., force Fc) may be applied to the lateral sides of collar 120 causing collar 120 to be squeezed along a circumference of the collar 120. In some embodiments, the axial pullout force (e.g., force F) does not result in collar 120 decoupling from second connector 140.

In some embodiments, collar 120 includes connecting arms 128 that are disposed proximate second end 123. Connecting arms 128 may include one or more protrusions

129 and mating portion 144 may include one or more recesses 158 configured to receive protrusions 129. For example, each recess 158 may be configured to receive and secure one protrusion 129. Collar 120 may be secured to second connector 140 by axially moving collar 120 towards mating portion 144 and orienting connecting arms 128 and with recesses 158 to allow protrusions 129 to be disposed within recess 158 thereby securing collar 120 to mating portion 144 and second connector 140. Collar 120 may be secured to second connector 140 and be prevented from axially moving relative to second connector 140 due to protrusions 129 being secured within recesses 158.

Collar 120 may further include cavities 127 configured to receive extending arms 148 of body 142. In some embodiments, when collar 120 is coupled to second connector 140, extending arms 148 are disposed within and/or extend through cavity 127. Cavities 127 may be configured to align and secure collar 120 with second connector 140.

Collar 120 may be decoupled from second connector 140 (e.g., mating portion 144) by providing a compressive force (e.g., force Fc) to collar 120 at or proximate to connecting arms 128. Providing force Fc at or proximate connecting arms 128 may cause connecting arms 128 to radially deflect outwards and may cause protrusions 129 move away and no longer be disposed within recess 158, allowing collar 120 to axially move along central axis A-A relative mating portion 144 and second connector 140. Axially moving collar 120 along central axis A-A and away from mating portion 144 results in extending arms 148 being withdrawn from cavities 127.

Figure 7A:
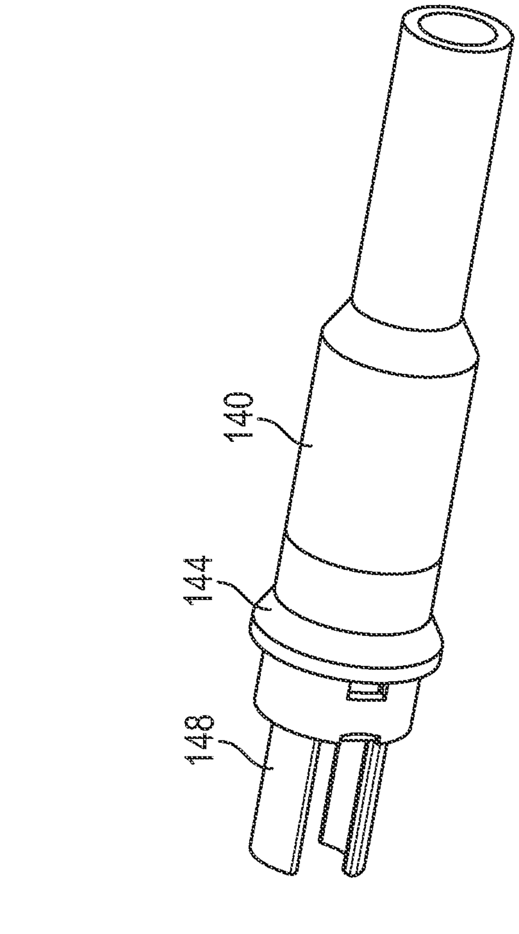
FIG. 7A is a top perspective view of the coupler assembly of FIG. 1A showing the collar removed and the first connector coupled to the thread, in accordance with some embodiments of the present disclosure.
Figure 7A:
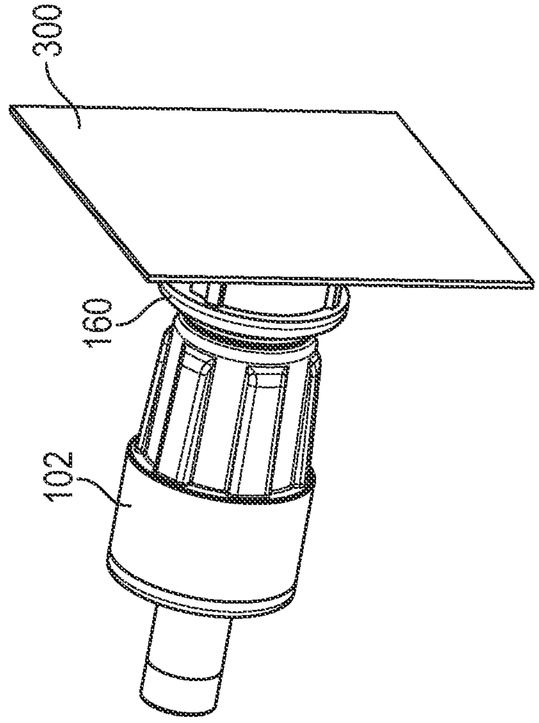

FIG. 7A is a top perspective view of the coupler assembly of FIG. 1A showing the collar removed and the first connector coupled to the thread, in accordance with some embodiments of the present disclosure. FIG. 7B is a cross sectional side view of the coupler assembly of FIG. 7A.

Referring to FIGS. 7A-7B, once collar 120 is decoupled from second connector 140, collar 120 may be discarded and first connector 102 may be sterilized using sterilizing device 300. Sterilizing device 300 may be an alcohol wipe, an iodine wipe, a sterilizing spray, an ultraviolet light generating device, or any other type of device configured to sterilize first connector 102. Sterilizing device 300 may be used to sterilizing first end 101, coupling portion 105, and thread 160. Alternatively, sterilizing device 300 is used to sterilize thread 160 and at least a substantial portion of first connector 102. Sterilizing device 300 may be configured to remove any contaminants, bacteria, viruses, and/or debris from first connector 102 prior to recoupling first connector 102 to a collar, connector, or other components.

Figure 8A:
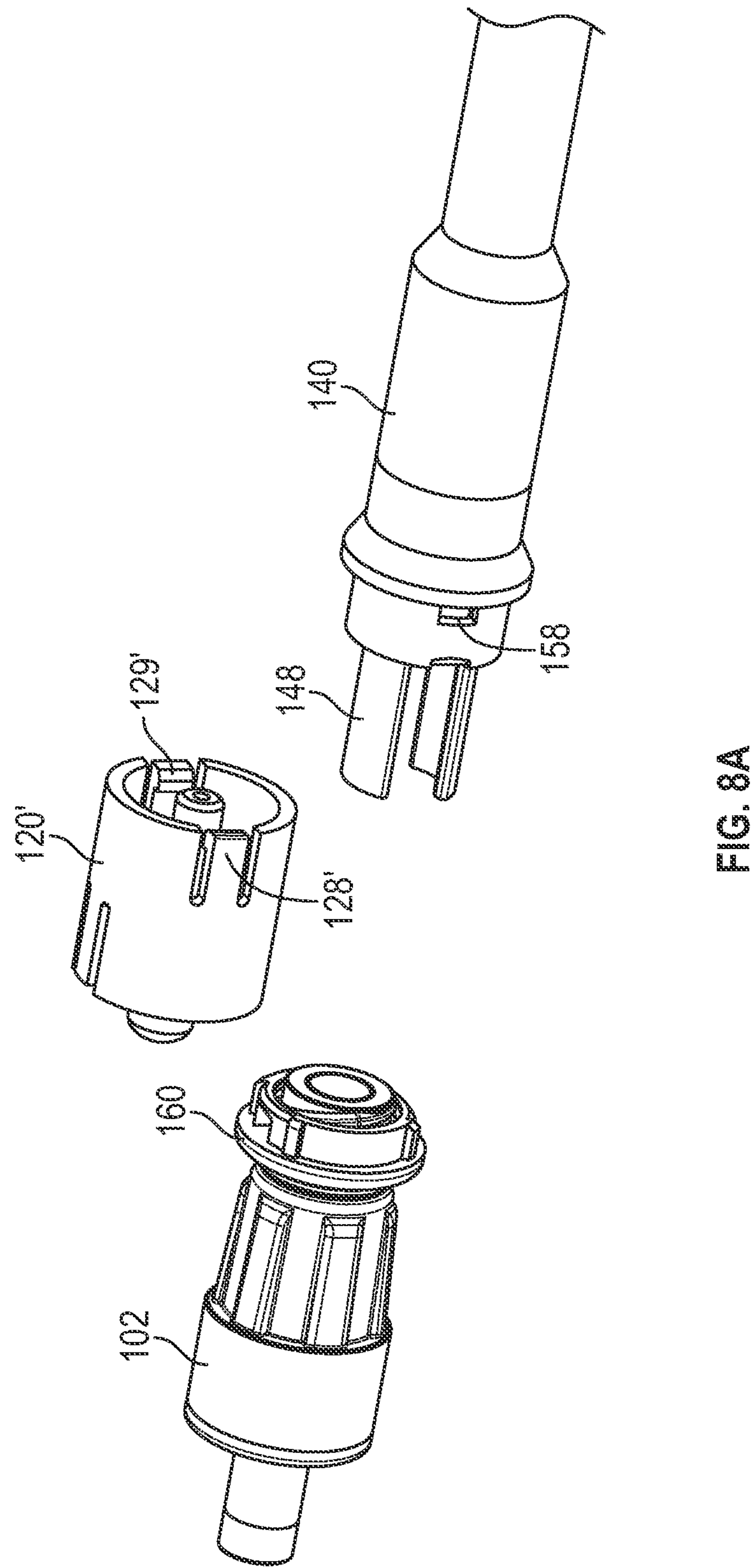
FIG. 8A is a top perspective view of the coupler assembly of FIG. 1A showing the thread coupled to the first connector and the collar removed and replaced with a replacement collar, in accordance with some embodiments of the present disclosure.
Figure 8B:
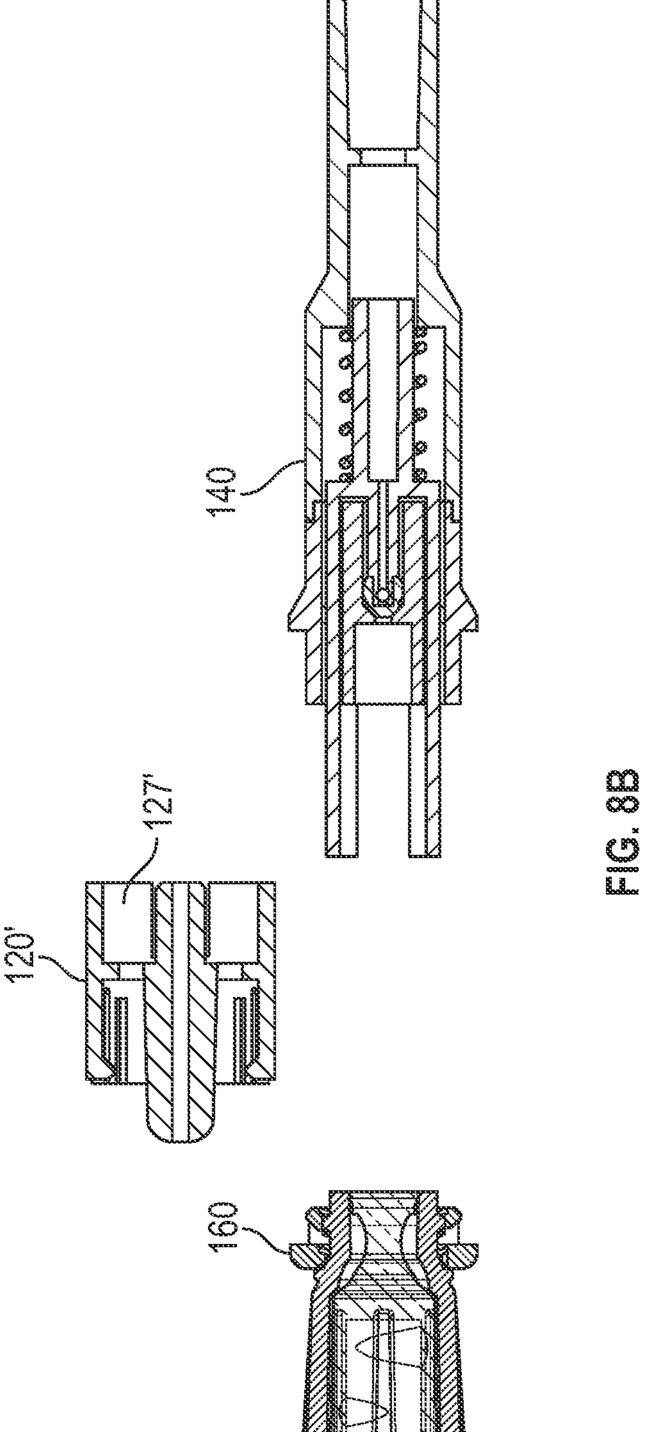
FIG. 8B is a cross sectional side view of the coupler assembly of FIG. 8A.
Figure 9A:
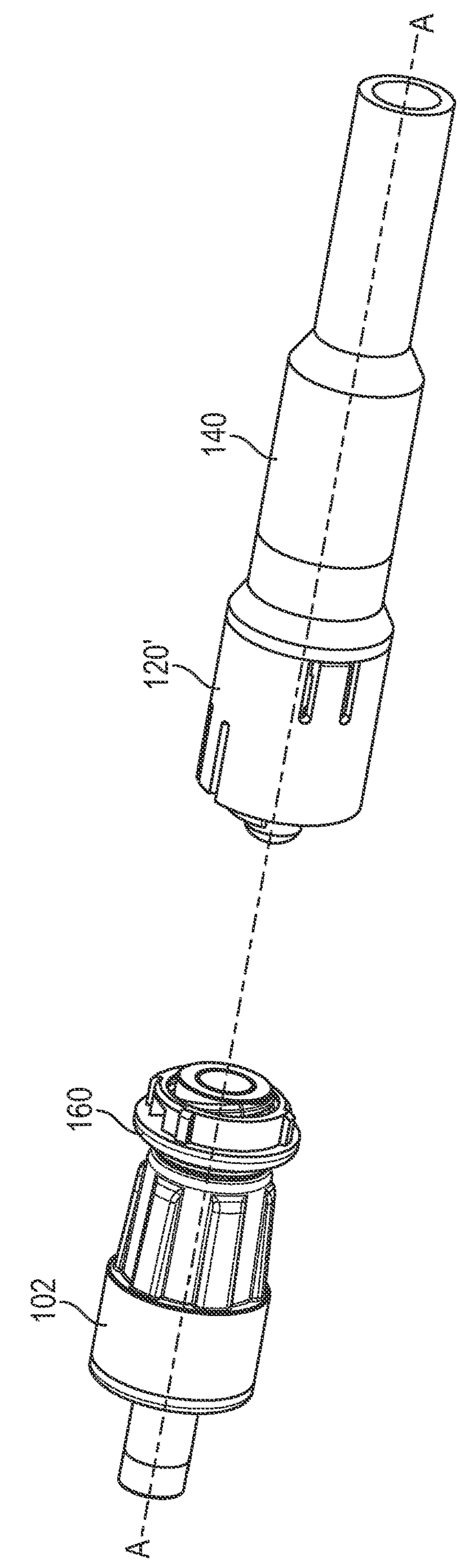
FIG. 9A is a top perspective view of the coupler assembly of FIG. 1A showing the first connector coupled to the thread and decoupled from the second connector, and the collar replaced with a replacement collar, in accordance with some embodiments of the present disclosure.
Figure 9B:
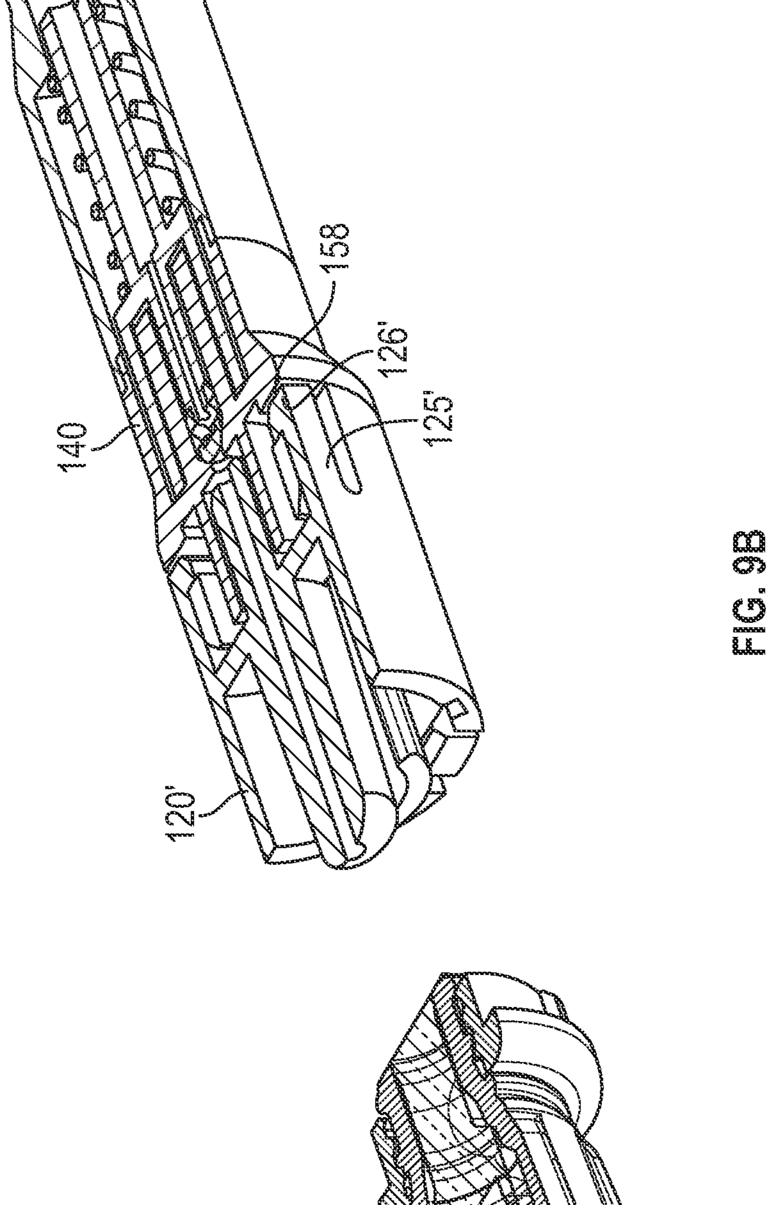
FIG. 9B is a cross sectional top perspective view of the coupler assembly of FIG. 9A.

FIG. 8A is a top perspective view of the coupler assembly of FIG. 1A showing the thread coupled to the first connector and the collar removed and replaced with a replacement collar, in accordance with some embodiments of the present disclosure. FIG. 8B is a cross sectional side view of the coupler assembly of FIG. 8A. FIG. 9A is a top perspective view of the coupler assembly of FIG. 1A showing the first connector coupled to the thread and decoupled from the second connector, and the collar replaced with a replacement collar, in accordance with some embodiments of the present disclosure. FIG. 9B is a cross sectional top perspective view of the coupler assembly of FIG. 9A.

Referring to FIGS. 8A-9B, collar 120 may be decoupled from second connector 140 and discarded. A replacement sterile collar 120' may be retrieved to couple to second connector 140. In some embodiments, collar 120' is coupled to second connector 140 similar to when coupler assembly 100 is in the third configuration. Collar 120' may be coupled to second connector 140 and the flow of fluid through second connector 140 may resume to allow the flow of fluid to pass through second connector 140, collar 120', and first connector 102.

In some embodiments, collar 120' is coupled to second connector 140 similar to collar 120. Collar 120' may be substantially the same as collar 120. Collar 120' may be aligned with extending arms 148 such that collar 120' is axially aligned along central axis A-A and extending arms 148 are aligned with cavity 127'. In some embodiments, collar 120' is coupled to second connector 140 (similar to collar 120) such that extending arms 148 are disposed or extend through cavity 127'. In some embodiments, protrusions 129' of connecting arms 128' are disposed within recess 158 to couple and secure collar 120' to second connector 140.

Figure 10:
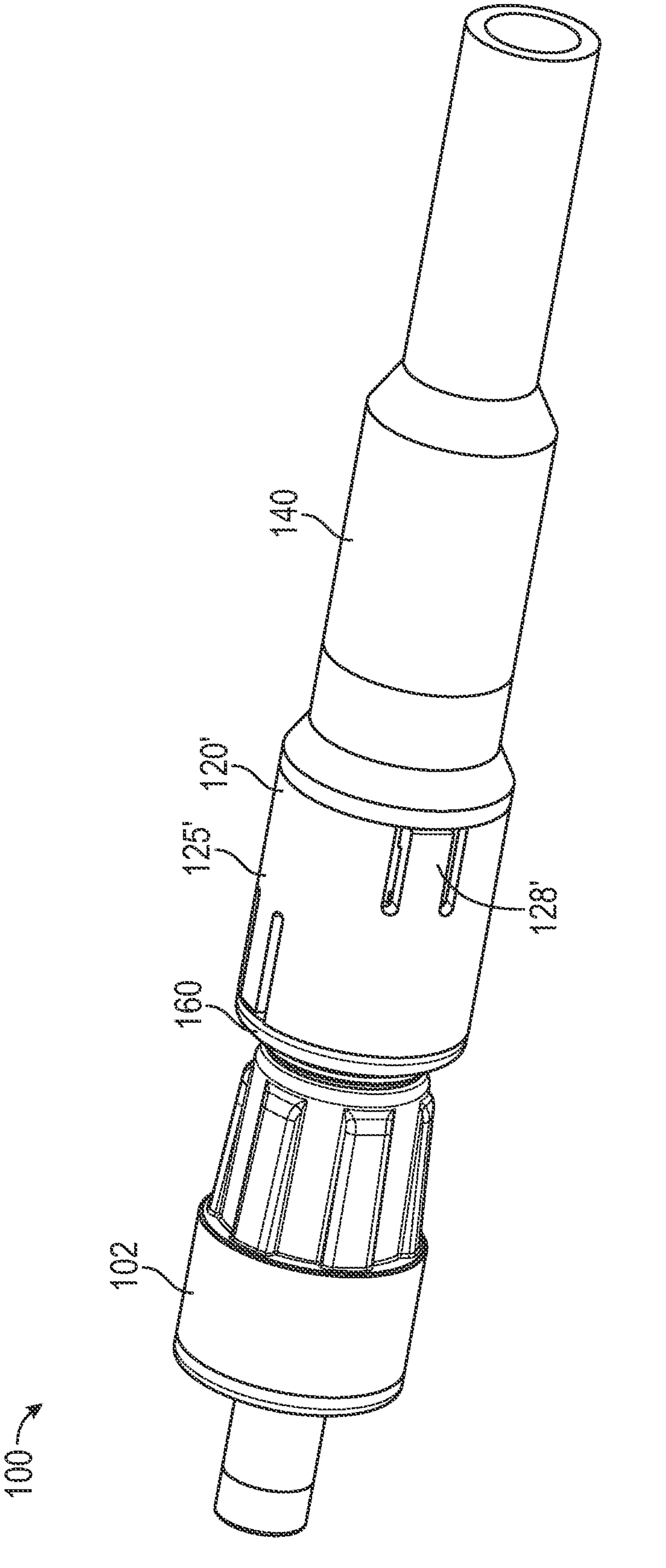
FIG. 10 is a top perspective view of the coupler assembly of FIG. 1A showing the first connector coupled to the thread, which is coupled to the replacement collar and the second connector, in accordance with various aspects of the present disclosure.

FIG. 10 is a top perspective view of the coupler assembly of FIG. 1A showing the first connector coupled to the thread, which is coupled to the replacement collar and the second connector, in accordance with various aspects of the present disclosure.

Referring to FIG. 10, collar 120', which is coupled to second connector 140, may be coupled to thread 160, which is coupled to first connector 102. In some embodiments, collar 120' is configured to couple second connector 140 to first connector 102 to allow for fluid communication between second connector 140 and first connector 102. In some embodiments, collars 120' is coupled to thread 160 by applying an axial force along central axis A-A. In applying an axial force, engaging arms 125 may be configured to engage with thread 160' similar to how collar 120 engages and couples with thread 160. In some embodiments, collar 120' is recoupled to thread 160 and first connector 102 by applying an axial force along central axis A-A to cause engaging arms 125' to radially deflect outwards and then engage with notch 163 of thread 160 to secure collar 120' to thread 160 and first connector 102. In some embodiments, collar 120' couples second connector 140 to first connector 102 via thread 160 similar to when coupler assembly 100 is in the first configuration. In some embodiment, collar 120' couples to thread 160 via snap connection (e.g., friction fitting thread 160 within collar 120').

Figure 11:
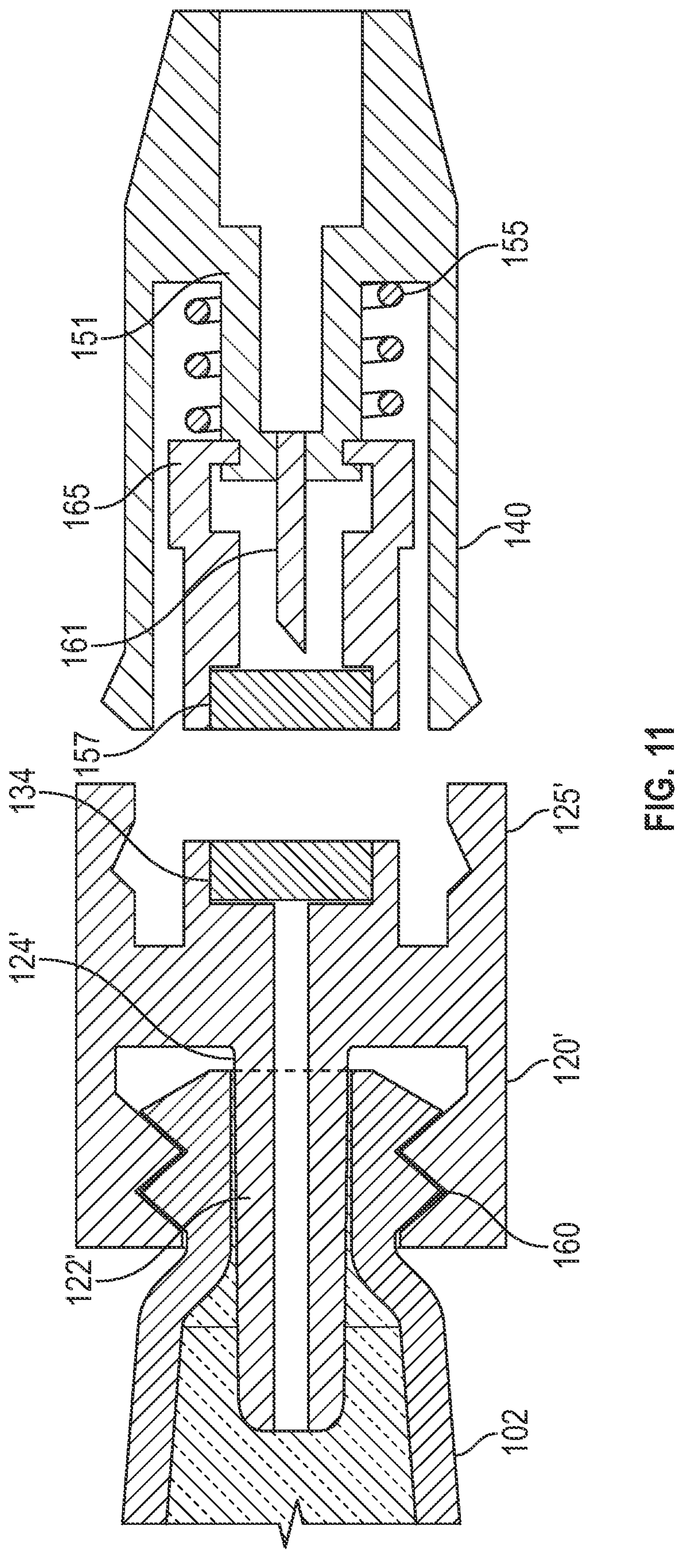
FIG. 11 is a cross sectional side view of a coupler assembly, in accordance with various aspects of the present disclosure.

FIG. 11 is a cross sectional side view of a coupler assembly, in accordance with various aspects of the present disclosure.

Referring to FIG. 11, collar 120' includes valve 134 and second connector 140 includes valve 157. Valve 134 may be configured to seal collar 120'. For example, valve 134 may be configured to allow and prevent flow through luer channel 122'. Valve 157 may be configured to seal second connector 140, similar to valve 153. In some embodiments, second connector includes body 165, which is similar to body 142, and pin 161, which is similar to pin 152. Pin 161 may be a needle that is in fluid communication with tube 151.

In some embodiments, body 165 is configured to axially move relative to pin 161. For example, body 165 may be biased away from tube 151 by biasing element 155 and body 165 may axially move towards tube 151 due to an axial force being applied to body 165, resulting in biasing element 155 compressing. Biasing element 155 compressing allows body 165 to axially move towards pin 161.

In some embodiments, collar 120' is coupled to first connector 102 via thread 160 and is configured to be coupled to second connector 140. Upon coupling of collar 120' to second connector 140, collar 120' may abut body 165 and apply an axial force on body 165 causing body 165 to move towards tube 151 relative to pin 161. For example, valve 157 may be disposed within or coupled to body 165 and abutting valve 134 of collar 120' against valve 157 of second connector 140 results in collar 120' (e.g., valve 134) applying an axial force against valve 157 of body 165. Body 165 moving relative to pin 161 towards tube 151 may cause pin 161 to be inserted into and extend through valve 157 as collar 120' couples to second connector 140.

Upon the coupling of collar 120' to second connector 140, pin 161 may extend through valve 157 and through valve 134 resulting in pin 161 being disposed within luer channel 122'. Pin 161 being disposed within luer channel 122' may allow for collar 120' (which is in fluid communication with first connector 102) to be in fluid communication with second connector 140. This results in first connector 102 being in fluid communication with second connector 140 via collar 120'. Collar 120' may be coupled to second connector 140 via engaging arms 125'. For example, collar 120' may be snap fitted or friction fitted with second connector 140 via engaging arms 125' to coupled and secure collar 120' to second connector 140.

The disclosures described herein include at least the following clauses:

Clause 1: A coupler comprising a first connector having a first end, a second end opposite the first end, and a valve extending from an area proximate the second end to an area proximate the first end, a second connector having a mating portion and a connecting portion opposite the mating portion, and a collar having a connecting end detachably coupled to the mating portion of the second connector and an engaging end disposed opposite the connecting end, the collar including a thread detachably coupled to the engaging end, the thread configured to couple to at least a portion of the first connector to detachably couple the first connector to the collar and the second connector such that the first connector, the collar, and the second connector form a fluid pathway, wherein, when the first connector and the thread are coupled together, the first connector and the thread are configured to decouple from the collar while the collar remains coupled to the second connector.

Clause 2: The coupler of clause 1, wherein the first connector and the thread are configured to decouple from the collar in response to a pullout force exceeding a predetermined threshold force.

Clause 3: The coupler of clause 2, wherein the collar is configured to decouple from the second connector in response to a compressive force, the compressive force being different than the pullout force.

Clause 4: The coupler of clause 2, wherein the pullout force is a force applied to the first connector along a central axis of the first connector.

Clause 5: The coupler of clause 4, wherein the central axis extends at least along a length of the first connector.

Clause 6: The coupler of clause 4, wherein the central axis extends through the first connector, the thread, the collar, and the second connector when the first connector is coupled to the collar via the thread and the collar is coupled to the second connector.

Clause 7: The coupler of clause 2, wherein the first connector is coupled to the thread and is configured to remain coupled to the collar when the pullout force does not exceed the predetermined threshold force.

Clause 8: The coupler of clause 1, wherein the collar includes a luer extending from at least the engaging end to at least the connecting end and the valve is configured to receive the luer when the first connector is coupled to the collar.

Clause 9: The coupler of clause 8, wherein the luer is at least partially disposed within the second connector when the collar is coupled to the second connector.

Clause 10: The coupler of clause 8, wherein a portion of the luer is disposed within the mating portion of the second connector when the collar is coupled to the second connector.

Clause 11: The coupler of clause 1, wherein the second connector includes a body disposed within the second connector, the body having a tube at least partially extending into the connecting portion and a pin at least partially extending into the mating portion.

Clause 12: The coupler of clause 11, wherein the body includes an extending arm extending from the body away from the tube, the extending arms configured to extend at least partially into the collar when the collar is coupled to the second connector.

Clause 13: The coupler of clause 1, wherein the thread is threaded to threadably engage with the second end of the first connector.

Clause 14: The coupler of clause 1, wherein the collar includes an engaging arm detachably coupling the collar to the thread, the engaging arms configured to release the thread when the thread is coupled to the first connector and a pullout force is applied to the first connector that exceeds a predetermined threshold force.

Clause 15: The coupler of clause 1, wherein the collar includes a connecting arm detachably coupling the collar to the mating portion of the second connector, the connecting arms configured to decouple from the mating portion.

Clause 16: The coupler of clause 1, wherein the coupler has a first configuration and in the first configuration the first connector is decoupled from the collar, the thread is detachably coupled to the collar, and the collar is coupled to the second connector.

Clause 17: The coupler of clause 1, wherein the coupler has a second configuration and in the second configuration the first connector is coupled to the thread, the thread is coupled to the collar, and the collar is coupled to the second connector.

Clause 18: The coupler of clause 1, wherein the coupler has a third configuration and in the third configuration the first connector is coupled to the thread, the first connector and the thread are disconnected from the collar, and the collar is coupled to the second connector.

Clause 19: The coupler of clause 1, wherein the coupler has a fourth configuration and in the fourth configuration the first connector is coupled to the thread, the first connector and the thread are disconnected from the collar, and the collar is decoupled from the second connector.

Clause 20: The coupler of clause 1, wherein when the first connector couples to the collar, the thread engages with the second end of the first connector to secure the first connector to the collar.

Clause 21: The coupler of clause 1, wherein the first connector is coupled to a first portion of tubing at the first end and the second connector is coupled to a second portion of tubing at the connecting portion.

Clause 22: The coupler of clause 1, wherein the mating portion has a maximum diameter greater than a maximum diameter of the connecting portion.

Clause 23: A coupler comprising a first connector having a first end, a second end opposite the first end, and a valve disposed within the first connector, the first end including threads, a second connector having a mating portion, a connecting portion opposite the mating portion, and a body at least partially disposed between the mating portion and the connecting portion, and a collar having at least one connecting arm at a connecting end, and at least one engaging arm at an engaging end, the connecting portion being disposed opposite the engaging end, the collar having a thread disposed at the engaging end, wherein the collar is configured to couple the first connector to the second connector to form a fluid pathway, wherein, when the first connector is coupled to the thread, the first connector and the thread configured to decouple from the collar and the second connector in response to a pullout force exceeding a predetermined threshold force.

Clause 24: A coupler comprising a first connector having a first end, a second end opposite the first end, and a valve disposed within the first connector, the first end including threads, a second connector having a mating portion, a connecting portion opposite the mating portion, and a body at least partially disposed between the mating portion and the connecting portion the body having a valve configured to fluidly seal the second connector and configured to axially move relative to the mating portion and the connecting portion, and a collar having a luer disposed within, at least one connecting arm at a connecting end, and at least one engaging arm at an engaging end, the connecting portion being disposed opposite the engaging end, the collar having a thread disposed at the engaging end, the thread configured to releasably couple to the at least one engaging arm, wherein the thread is configured to mate with the threads of the first end, wherein the collar is configured to couple the first connector to the second connector to form a fluid pathway such that a first portion of the luer is disposed within the first connector and a second portion of the luer opposite the first portion is disposed within the second connector, wherein, when the first connector is coupled to the thread, the first connector and the thread configured to decouple from the collar and the second connector in response to a pullout force exceeding a predetermined threshold force, wherein a central axis extends through the first connector, the thread, the collar, and the second connector when the collar is coupled to the first connector and the second connector, wherein, when the first connector is coupled to the thread and the first connector and the thread are decoupled from the collar, the collar is configured to decouple form the second connector in response to a compressive force, the compressive force being different than the pullout force.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A coupler comprising:

a first connector having a first end, a second end opposite the first end, and a valve extending from an area proximate the second end to an area proximate the first end;

a second connector having a mating portion and a connecting portion opposite the mating portion;

a collar having a connecting end detachably coupled to the mating portion of the second connector and an engaging end disposed opposite the connecting end; and a thread, wherein, when the coupler is in a first configuration, the second connector is coupled to the collar, the thread is detachably coupled to the engaging end of the collar, and the first connector is decoupled from the collar, wherein, when the coupler is in a second configuration, the thread is coupled to at least a portion of the first connector to detachably couple the first connector to the collar and the second connector such that the first connector, the collar, and the second connector form a fluid pathway, wherein, when the coupler is in a third configuration, the first connector and the thread are coupled together, the first connector and the thread are decoupled from the collar while the collar remains coupled to the second connector, wherein, when the coupler is in a fourth configuration, the second connector and the collar are decoupled.

2. The coupler of claim 1, wherein the coupler is configured to transition from the second configuration to the third configuration in response to a pullout force exceeding a predetermined threshold force.

3. The coupler of claim 2, wherein the coupler is configured to transition from the third configuration to the fourth configuration in response to a compressive force, the compressive force being different than the pullout force and applied to the collar along a circumference of the collar.

4. The coupler of claim 2, wherein the pullout force is a force applied to the first connector along a central axis of the first connector.

5. The coupler of claim 4, wherein the central axis extends at least along a length of the first connector when the coupler is in the first configuration, the second configuration, the third configuration, and the fourth configuration.

6. The coupler of claim 4, wherein the central axis extends through the first connector, the thread, the collar, and the second connector when the coupler is in the second configuration.

7. The coupler of claim 2, wherein the coupler is configured to remain in the second configuration when the pullout force does not exceed the predetermined threshold force.

8. The coupler of claim 1, wherein the collar includes a luer extending from at least the engaging end to at least the connecting end and the valve is configured to receive the luer when the first connector is coupled to the collar.

9. The coupler of claim 8, wherein the luer is at least partially disposed within the second connector when the collar is coupled to the second connector.

10. The coupler of claim 1, wherein the second connector includes a housing and a body disposed within the housing, the body having a tube at least partially extending into the connecting portion and a pin at least partially extending into the mating portion.

11. The coupler of claim 10, wherein the body includes an extending arm extending from the body away from the tube, the extending arm configured to extend at least partially into the collar when the collar is coupled to the second connector.

12. The coupler of claim 1, wherein the collar includes an engaging arm detachably coupling the collar to the thread when the coupler is in the first configuration and the second configuration, and the engaging arms are configured to release the thread when the coupler transitions from the second configuration to the third configuration.

13. The coupler of claim 1, wherein the collar includes a connecting arm detachably coupling the collar to the mating portion of the second connector when the coupler is in the first configuration, the second configuration, and the third configuration, and the connecting arms are configured to decouple from the mating portion when the coupler transitions from the third configuration to the fourth configuration.

14. The coupler of claim 1, wherein, when the coupler is in the fourth configuration, the first connector is coupled to the thread and the first connector and the thread are disconnected from the collar.

15. The coupler of claim 1, wherein the first connector is coupled to a first portion of tubing at the first end and the second connector is coupled to a second portion of tubing at the connecting portion.

16. The coupler of claim 1, wherein the second connector comprises a pin and a sealing valve disposed at an end of the pin and within the mating portion.

17. The coupler of claim 16, wherein the pin and the sealing valve are axially movable along a central axis of the second connector relative to an opening in the mating portion to selectively seal the opening.

18. The coupler of claim 17, wherein the pin and the seal abut the opening when the coupler is in the fourth configuration.

19. A coupler comprising:

a first connector having a first end, a second end opposite the first end, and a valve disposed within the first connector, the first end including threads;

a second connector having a mating portion, a connecting portion opposite the mating portion, and a body at least partially disposed between the mating portion and the connecting portion;

a collar having at least one connecting arm at a connecting end, and at least one engaging arm at an engaging end, the connecting portion being disposed opposite the engaging end; and a thread coupled to the engaging end via the at least one engaging arm, wherein the collar is configured to couple with the threads of the first end of the first connector to form a fluid pathway between the first connector and the second connector, wherein the first connector is configured to couple to the thread via the threads of the first end of the first connector, wherein the first connector and the thread are configured to decouple from the collar and the second connector in response to a pullout force that deflects the at least one engaging arm to decouple the thread and the engaging end, the pullout force exceeding a predetermined threshold force.

20. A coupler comprising:

a first connector having a first end, a second end opposite the first end, and a valve disposed within the first connector, the first end including threads;

a second connector having a mating portion, a connecting portion opposite the mating portion, and a body at least partially disposed between the mating portion and the connecting portion the body having a valve configured to fluidly seal the second connector and configured to axially move relative to the mating portion and the connecting portion;

a collar having a luer disposed within, at least one connecting arm at a connecting end, and at least one engaging arm at an engaging end, the at least one connecting arm being releasably coupled to the mating portion; and a thread comprising a notch, releasably coupled to the at least one engaging arm via the notch, and configured to mate with the threads of the first end, wherein the collar is configured to couple the first connector to the second connector to form a fluid pathway such that a first portion of the luer is disposed within the first connector and a second portion of the luer opposite the first portion is disposed within the second connector, wherein, when the first connector is coupled to the thread, the first connector and the thread are configured to decouple from the collar and the second connector in response to a pullout force that deflects the at least one engaging arm away from the notch, the pullout force exceeding a predetermined threshold force, wherein the pullout force is applied along a central axis that extends through the first connector, the thread, the collar, and the second connector when the collar is coupled to the first connector and the second connector, wherein, when the first connector is coupled to the thread and the first connector and the thread are decoupled from the collar, the collar is configured to decouple from the second connector in response to a compressive force that deflects the at least one connecting arm away from the mating portion, the compressive force being different than the pullout force.

* * * * *